US006455513B1

(12) United States Patent
McGuigan et al.

(10) Patent No.: US 6,455,513 B1
(45) Date of Patent: *Sep. 24, 2002

(54) CHEMICAL COMPOUNDS

(75) Inventors: Christopher McGuigan, Cardiff (GB); Jan Balzarini, Heverlee (BE)

(73) Assignees: University College Cardiff Consultants Ltd., Cardiff (GB); Rega Foundation, Leuven (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/382,084

(22) Filed: Aug. 24, 1999

Related U.S. Application Data

(63) Continuation of application No. 08/913,639, filed as application No. PCT/GB96/00580 on Mar. 13, 1996, now abandoned.

(30) Foreign Application Priority Data

Mar. 13, 1995 (GB) .............................................. 9505025

(51) Int. Cl.$^7$ ...................... C07F 9/6561; C07F 9/6558; C07F 9/6512; A61K 31/685; A61P 31/18
(52) U.S. Cl. .......................... 514/81; 514/86; 544/105; 544/118; 544/243; 544/244
(58) Field of Search ...................... 514/81, 86; 544/243, 544/244, 105, 118

(56) References Cited

U.S. PATENT DOCUMENTS

| | | | |
|---|---|---|---|
| 5,591,851 A | 1/1997 | Alexander | 544/243 |
| 5,656,745 A | 8/1997 | Bischofberger et al. | 536/25.34 |
| 5,798,340 A | 8/1998 | Bischofberger et al. | 514/45 |

FOREIGN PATENT DOCUMENTS

| | | |
|---|---|---|
| WO | WO 95/07920 | 3/1995 |

OTHER PUBLICATIONS

McGuigan et al, FEBS Letters 351, 11, 1994.*
McGuigan et al, Bioorganic & Medicinal Chem Letters 2, 701, 1992.*
McGuigan et al, Antiviral Res. 17, 311, 1991.*
McGuigan et al, Antiviral Chem and Chemotherapy 7, 31, 1996.*
McGuigan et al, J. Med Chem 37, 3534, 1994.*
McGuigan et al, J. Med Chem 36, 1048, 1993.*
American Medical Association, "Drug Evaluations Manual", 1993, p. 1723, 1993.*
Munson, ed, "Principle of Pharmacology", Chapman and Hall, 1995, p. 1414, 1995.*
Wyngaarden, ed, "Cecil Textbook of Medicine", 19th Edition, p. 1801, 1993.*
Introduction to Organic Chemistry, Condon et al, (Holt, NY, 1980) p. 38.*
Chemistry of Organic Compounds, 2nd edition, Noller (Saunders Company, 1975) p. 52.*
Organic Chemistry, Morrison and Boyd (Allyn & Bacon, Inc, NYU, 1976) p. 84.*

* cited by examiner

*Primary Examiner*—Mark Berch
(74) *Attorney, Agent, or Firm*—Mathews, Collins, Shepherd & McKay, P.A.

(57) ABSTRACT

Aryl substituted phosphoryl derivatives of the formula

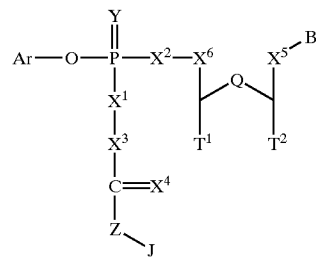

In which Ar is phenyl, naphthyl, or pyridyl, Y is O or S, $X^1$ is O, $NR^3$, S, $CR^3R^4$, $CR^3W^1$ or $CW^1W^2$, $X^2$ and $X^6$ are a bond or $X^6$ is $CH_2$ and $X^2$ is O, $NR^3$, S, $CR^3R^4$, $CR^3W^1$ or $CW^1W^2$, $R^3$ and $R^4$ are H, alkyl or phenyl, groups, $W^1$ and $W^2$ are heteroatoms, $X^3$ is alkylene, $X^4$ is oxygen or $CH_2$, $X^5$ is a bond or $CH_2$, Z is O, $NR^5$, S, alkyl or phenyl, $R^5$ is H, alkyl or phenyl, J is H, alkyl, phenyl, or a heterocyclic or polycyclic group, Q is O, $NR^6$, S, $CR^6R^7$, $CR^6W^3$ or $CW^3W^4$, $R^6$ and $R^7$ are H, alkyl, or phenyl, and $W^3$ and $W^4$ are hetero atoms, $T^1$ and $T^2$ are H or $CH_2R^8$, $R^8$ is H, OH or F, or $T^1$ and $T^2$ together are —CH=CH— or —C($R^9$)($R^{10}$)C($R^{11}$)($R^{12}$)—, $R^9$ is H, halogeno, CN, $NH_2$, CO-alkyl, or alkyl, $R^{10}$, $R^{11}$, and $R^{12}$ are H, $N_3$, halogen, CN, $NH_2$, CO-alkyl, or alkyl, and B is a purine or pyrimidine base, have antiviral activity, as for example against HIV. Particularly preferred are thymine and adenine derivatives of amino acid phenoxyphosphoroamides. A typical embodiment is 2',3'-dideoxy-2',3'-didehydrothymidine 5'-(phenyl methoxy alaninyl) phosphoroamidate which can be prepared from phenyl methoxy alaninyl phosphorochloridate and 2',3'-dideoxy-2',3'-didehydrothymidine.

33 Claims, No Drawings

CHEMICAL COMPOUNDS

CROSS REFERENCE TO RELATED APPLICATIONS

This application is a Continuation of Ser. No. 08,913,639, filed Feb. 2, 1998, now Abandoned, which isuuu a 371 of PCT/GB96/00580, filed Mar. 13, 1996.

FIELD OF THE INVENTION

The present invention relates to a new class of nucleoside analogues and their therapeutic use in the prophylaxis and treatment of viral infection, for example by human immunodeficiency virus (HIV), which is believed to be the aetiological agent in human acquired immunodeficiency syndrome (AIDS).

BACKGROUND OF THE INVENTION

There has been much interest in the use of nucleoside analogues as inhibitors of HIV. 2',3'-dideoxy-2',3'-didehydrothymidine (d4T) and 3'-azido-3'-deoxythymidine (AZT) are both known inhibitors of HIV [Hitchcock et al., Antiviral Chem. Chemother. (1991), 2, 125; Mansuri et al., Antimicrob. Agents Chemother., (1990), 34, 637.]. The inhibition of HIV by these, and other nucleoside analogues, is conventionally thought to depend upon conversion of the nucleoside analogue in vivo to the corresponding 5'-triphosphate by (host-cell) kinase enzymes. However, this absolute dependence upon (host-cell) kinase-mediated activation can lead to poor activity, the emergence of resistance, and clinical toxicity.

In order to reduce the dependence on kinase enzymes the use of masked phosphate pro-drugs of the bioactive nucleotide forms of several chemotherapeutic nucleoside analogues has been suggested [McGuigan et al., Nucleic Acids Res., (1989), 17, 6065; McGuigan et al., Ibid., (1989), 17, 7195; Chawla et al., J. Med. Chem., (1984), 27, 1733; Sergheraert et al., J. Med. Chem. (1993), 36, 826–830.]. In particular, McGuigan et al [J. Med. Chem. 36, 1048–1052 (1993)] have reported the preparation of aryl ester—phosphoramidate derivatives of AZT. In vitro evaluation of these compounds revealed the compounds to have anti-HIV activity. However, in "normal" thymidine kinase rich (TK$^+$) cells, the activity of such compounds was at least an order of magnitude less than the parent nucleoside AZT. Only in TK-deficient (TK$^-$) cells, in which the activity of the aryl ester—phosphoramidate derivatives was virtually maintained but the activity of AZT was reduced, did the activity of the derivatives exceed that of AZT.

McGuigan et al [Bioorganic & Medical Chemistry Letters, 3,(6), 1203–1206 (1993)] have also reported preparation of triester phosphate derivatives of d4T. Again, in vitro evaluation of these compounds revealed that whilst the compounds have significant anti-HIV activity, the activity is less than that of the parent nucleoside d4T in TK$^+$ cells.

Abraham and Wagner (Nucleosides and Nucleotides 13 (9). 1891–1903 (1994)) have reported the preparation of nucleoside phosphoramidate diesters and triesters but do not report any biological activity.

The acyclic nucleoside analogue 9(2-phosphonomethoxyethyly adenine (PMEA), and analogues thereof, have been demonstrated to show activity against herpes viruses and retroviruses including HIV (Calio et al., Antiviral Res., (1994), 23(1), 77–89; Balzarini et al., AIDS, (1991), 5(1), 21–28).

To date, the approach of providing masked phosphate pro-drugs has failed to enhance the anti-viral activities of the parent nucleoside analogues such as AZT and d4T in TK$^+$ cells. Furthermore, the emergence of resistance to the nucleoside analogues in their bioactive 5'-triphosphate form has rendered the reported masked phosphate pro-drugs and their parent nucleoside analogues potentially ineffective.

DESCRIPTION OF THE INVENTION

It has now been found that a particular class of masked nucleoside analogues are highly potent viral inhibitors in both TK$^-$ and TK$^+$ cells, and yet retain activity against nucleoside (e.g. d4T)-resistant virus.

According to the present invention there is provided a compound of the formula (1)

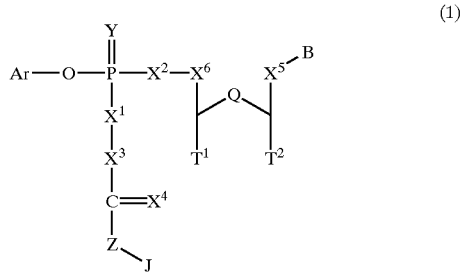

wherein Ar is an aryl group;

Y is oxygen or sulphur;

$X^1$ is selected from O, $NR^3$, S, $CR3R^4$, $CR^3W^1$ and $CW^1W^2$ where $R^3$ and $R^4$ are independently selected from hydrogen, alkyl and aryl groups; and $W^1$ and $W^2$ are heteroatoms;

$X^2$ and $Y^6$ together are direct bond; or X is $CH_2$ and $X^2$ is selected (independently of $X^1$) from O, $NR^3$, S, $CR^3R^4$, $CR^3W^1$ and $CW^1W^2$ where $R^3$ and $R^4$ are independently selected from hydrogen, alkyl and aryl groups; and $W^1$ and $W^2$ are heteroatoms;

$X^3$ is a alkylene of 1 to 6 carbon atoms (e.g., alkenyl);

$X^4$ is oxygen or $CH_2$;

$X^5$ may be absent or is $CH_2$;

Z is selected from O, $NR^5$, S, alkylene and arylene (e.g., alkenyl) groups, where $R^5$ is selected from hydrogen, alkyl and aryl groups;

J is selected from hydrogen, alkyl, aryl, heterocyclic and polycyclic groups;

Q is selected from O, $NR^6$, S, $CR^6R^7$, $CR6W^3$ and $CW^3W^4$ where $R^6$ and $R^7$ are independently selected from hydrogen, alkyl and aryl groups; and $W^3$ and $W^4$ are heteroatoms;

$T^1$ and $T^2$ are independently selected from hydrogen and $CH_2R^8$, where $R^8$ is selected from H, OH and F; or $T^1$ and $T^2$ are linked together and together are selected from the groups

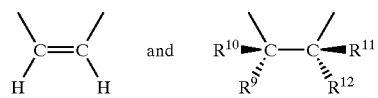

where $R^9$ is selected from H, halogen, CN, $NH_2$, CO-alkyl and alkyl; and $R^{10}$, $R^{11}$, $R^{12}$ are independently selected from H, $N_3$, halogen, CN, $NH_2$, CO-alkyl and alkyl;

B is a purine or pyrimidine base;

or a pharmaceutically acceptable derivative or metabolite thereof.

The compounds of the present invention are potent antiviral agents. In particular, they are highly active against HIV in both TK⁻ and TK⁺ cells. Particularly surprising is the activity of the compounds of the present invention against nucleoside-resistant HIV. These observations indicate that the activity of these compounds is not wholly dependent upon the conventional mode of action (requiring hydrolysis of the phosphate aryl ester and P-$X^1$ bonds followed by kinase-dependent conversion to the 5'-triphosphate derivative), but arises from an entirely different mode of action. The experimental data presented herein indicates that the compounds and metabolites of the present invention are directly acting as reverse transcriptase (RT) inhibitors via a previously unrecognised metabolic pathway and mechanism of action.

Reference in the present specification to an alkyl group means a branched or unbranched, cyclic or acyclic, saturated or unsaturated (e.g. alkenyl or alkynyl) hydrocarbyl radical. Where cyclic, the alkyl group is preferably $C_3$ to $C_{12}$, more preferably $C_5$ to $C_{10}$, more preferably $C_5$ to $C_7$. Where acyclic, the alkyl group is preferably $C_1$ to $C_{16}$, more preferably $C_1$ to $C_6$, more preferably methyl. Reference in the present specification to alkoxy and aryloxy groups means alkyl-O- and aryl-O- groups, respectively. Reference to alkanoyl and aryloyl groups means alkyl-CO- and aryl-CO-, respectively.

Reference in the present specification to an aryl group means an aromatic group, such as phenyl or naphthyl, or a heteroaromatic group containing one or more, preferably one, heteroatom, such as pyridyl, pyrrolyl, furanyl and thiophenyl. Preferably, the aryl group comprises phenyl or substituted phenyl.

The alkyl and aryl groups may be substituted or unsubstituted, preferably unsubstituted. Where substituted, there will generally be 1 to 3 substituents present, preferably 1 substituent. Substituents include halo, halomethyl (such as $CF_3$ and $CCl_3$), oxo, hydroxy, carboxy, carboxyalkyl, alkoxy, alkanoyl, alkanoyloxy, arloxy, arloyl, aryloyloxy, amino, alkylamino, dialkylamino, cyano, azide, nitro, thiol, alkylthiol, sulphonyl, sulphoxide, heterocyclic, alkyl, benzyl, and aryl (such as phenyl and substituted phenyl).

Reference in the present specification to heterocyclic groups means groups containing one or more, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxalinyl, chromenyl, chromanyl, isochromanyl and carbolinyl.

References in the present specification to polycyclic groups means a group comprising two or more non-aromatic carbcyclic or heterocyclic rings which may themselves be substituted.

Reference in the present specification to halogen means a fluorine, chlorine, bromine or iodine radical, preferably fluorine or chlorine radical.

The group Ar comprises a substituted or unsubstituted aryl group, wherein the term "aryl group" and the possible substitution of said group is as defined above. Preferably, Ar is a substituted or unsubstituted phenyl group. Particularly preferred substituents are election withdrawing groups such as halogen (preferably chlorine or fluorine), trihalomethyl (preferably trifluoromethyl), cyano and nitro groups.

Preferably, Ar is phenyl, 3,5-dichloro-phenyl, p-trifluoromethyl-phenyl, p-cyano-phenyl, or p-nitro-phenyl.

Y may be oxygen or sulphur. Preferably, Y is oxygen.

$X^1$ is from O, $NR^3$, S, $CR^3R^4$, $CR^3W^1$ and $CW^1W^2$ where $R^3$ and $R^4$ are independently selected from hydrogen, alkyl and aryl groups; and $W^1$ and $W^2$ are heteroatoms. Preferably, $X^1$ is selected from O, S and $NR^3$. Preferably, $X^1$ is $NR^3$. When present, $R^3$ is preferably H. When present, $W^1$ and $W^2$ may independently comprise any heteroatom such as a halogen, preferably fluorine. fluorine $X^2$ and $X^6$ together are a direct bond; or $X^6$ is $CH_2$ and $X^2$ is selected (independently of $X^1$) from O, $NR^3$, S, $CR^3R^4$, $CR3W^1$ and $CW^1W^2$ where $R^3$ and $R^4$ are independently selected from H, alkyl and aryl groups; and $W^1$ and $W^2$ are heteroatoms. When present, $X^2$ is preferably oxygen. When present, $R^3$ is preferably H. When present $W^1$ and $W^2$ may independently comprise any heteroatom such as halogen, preferably fluorine.

$X^4$ is oxygen or $CH_2$. Preferably, $X^4$ is oxygen.

$X^5$ may be absent or is $CH_2$.

Z may comprise O, $NR^5$, S, alkyl e.g. alkenyl or aryl groups, where $R^5$ is selected from H, alkyl and aryl groups. Preferably, Z is O or $NR^5$. Preferably, $R^3$ is hydrogen. Most preferably, Z is oxygen.

J is selected from hydrogen, alkyl, aryl, heterocyclic and polycyclic groups. Preferably, J is a substituted or unsubstituted alkyl group. Preferably, J is a substituted or unsubstituted $C_{1-6}$ alkyl group, preferably a benzyl or methyl group. "$X^3$ is a $C_{1-6}$ alkylene group. $X^3$ may be a $C_{1-6}$ substituted or unsubstituted, branched or unbranched, methylene chain." Preferably, $X^3$ is a group $CR^1R^2$ where $R^1$ and $R^2$ are indepedently selected from hydrogen, alkyl and aryl groups. Preferably, at least one of $R^1$ and $R^2$ is hydrogen. It will be appreciated that if $R^1$ and $R^2$ are different, the carbon atom to which they are bonded is an asymmetric centre. The stereochemistry at this site may be R or S or mixed. When one of $R^1$ and $R^2$ is hydrogen, the stereochemistry is preferably S.

Q is selected from O, $NR^6$, S, $CR^6R^7$, $CR^6W^3$ and $CW^3W^4$, where $R^6$ and $R^7$ are independently selected from hydrogen, alkyl and aryl groups; and $W^2$ and $W^3$ are heteroatoms such as halogen atoms, preferably fluorine. Preferably, Q is O, S, $CH_2$ or $CF_2$. Most preferably, Q is oxygen.

$T^1$ and $T^2$ are independently selected from hydrogen and $CH_2R^4$ where $R^8$ is selected from H, OH and F; or $T^2$ and $T^2$ are linked together and together are selected from the groups:

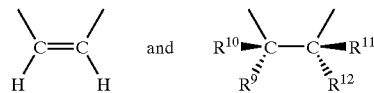

where $R^9$ is selected from H, halogen, CN, $NH_2$, CO-alkyl, and alkyl, preferably $R^9$ is H or F; and $R^{10}$, $R^{11}$, and $R^{12}$ are independently selected from H, $N_3$, halogen, CN, $NH_2$, CO-alkyl, and alkyl, preferably $R^{10}$, $R^{11}$ and $R^{12}$ are independently selected from H, F and $N_3$. It will be appreciated that $R^9$ corresponds to the 3'-α position and $R^{10}$ corresponds to the 3'-β position. Preferably, $T^1$ and $T^2$ are linked together and together form the group:

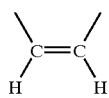

B is a monovalent radical of unsubstituted thymine, cytosine, adenine, or guanine, or a monovalent radical of substituted uracil, thymine, cytosine, adenine, or guanine in which th[0085] substituents are as defined above; e.g., halo, halomethyl, oxo, hydroxy, carboxy, carboxyalkyl, alkoxy, alkanoyl, alkanoyloxy, arloxy, aryloyl, aryloyloxy, amino, alkylamino, dialkylamino, cyano, azide, nitro, thiol, alkylthiol, sulphonyl, sulphoxide, heterocyclic, alkyl, benzyl, and aryl. Preferably, B is adenine or thymine.

Preferably, the present invention provides a compound of formula (2)

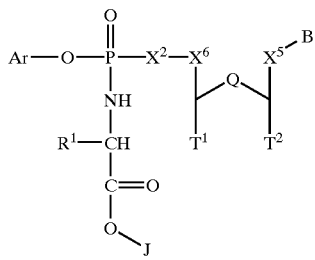

(2)

wherein Ar, $R^1$, J, $X^2$, $X^5$, $X^6$, Q, $T^1$, $T^2$ and B are as defined above; or a pharmaceutically acceptable derivative or metabolite thereof.

It will be appreciated that the group —NH—CHR$^1$—CO$_2$J corresponds to a carboxy-protected α-amino acid. Preferably, the group $R^1$ corresponds to the side chain of a naturally occurring amino acid such as alanine ($R^1$ is methyl), arginine ($R^1$ is 3-guanidinopropyl), asparagine ($R^1$ is carbamoylethyl), asparatic acid ($R^1$ is carboxymethyl), cysteine ($R^1$ is mercaptomethyl), cystine 9$R^1$ is 2-amino-2-carboxyethyldithiomethyl), glycine ($R^1$ is hydrogen), glutamic acid ($R^1$ is 2-carboxyethyl), glutamine ($R^1$ is 2-carbamoylethyl), hystidine ($R^1$ is 1H-imidazolemethyl), isoleucine ($R^1$ is but-2-yl), leucine ($R^1$ is butyl), lysine ($R^1$ is 4-aminobutyl), methionine ($R^1$ is 2-methylthioethyl), phenylalanine ($R^1$ is benzyl), serine ($R^1$ is hydroxymethyl), threonine ($R^1$ is 1-hydroxyethyl), tryptophan ($r^1$ is 1H-indol-3-ylemthyl), tyrosine ($R^1$ is 4-hydroxybenzyl), and valine ($R^1$ is prop-2-yl). Preferably $R^1$ is Me or PhCh$_2$ corresponding to the side chain of alanine or phenylalanine, respectively. Preferably, the stereochemistry at the asymmetric center —CHR$^1$— corresponds to an L-amino acid.

According to one preferred embodiment, the present invention provides a compound of formula (3):

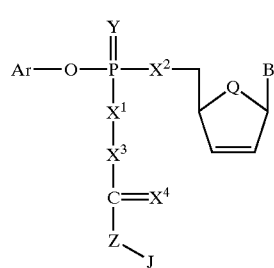

(3)

wherein Ar, Y, $X^1$, $X^2$, $X^3$, $X^4$, Z, Q and B are as defined above.

More preferably, the invention provides a compound, according to formula (3), of formula (4):

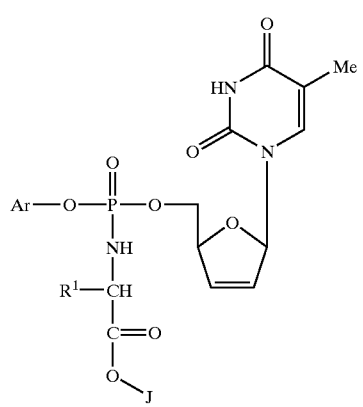

(4)

wherein Ar, $R^1$ and J are as defined above; or a pharmaceutically acceptable derivative or metabolite thereof. Preferably, the invention provides a compound of formula (4) in which Ar, $R^1$ and J are defined in accordance with Table 1.

TABLE 1

| Compound Reference | Ar | $R^1$ | J |
|---|---|---|---|
| 323 | 4-EtPh | Me | Me |
| 324 | Ph | Me | Me |
| 327 | 4-FPh | Me | Me |
| 526 | 3-CF$_3$Ph | Me | Me |
| 546 | 3,5-Cl$_2$Ph | Me | Me |
| 730 | Ph | Me | Bzl |
| 776 | 2,4-Br$_2$Ph | Me | Me |
| 779 | F$_5$Ph | Me | Me |
| 862 | Ph | Me | Hexyl |
| 863 | Ph | Bzl | Me |
| 864 | Ph | CH$_2$iPr | Me |
| 865 | Ph | iPr | Me |
| 866 | Ph | H | Me |
| 867 | Ph | [CH$_2$]$_2$SMe | Me |
| 868 | 2,4Br$_2$Ph | Me | Bzl |
| 877 | Ph | Bzl | Bzl |
| 878 | Ph | Bzl | tBu |
| 892 | Ph | Me | Cyclohexyl |
| 893 | Ph | Me | tBu |
| 1078 | Ph | CH$_2$CO$_2$H | Me |
| 1214 | Ph | CH$_2$CH$_2$CH$_2$NHC[NH$_2$]NH | Me |
| 1218 | Ph | Me | n-Pent |
| 1219 | Ph | Me | neo-Pent |
| 1226 | Ph | Me | 1-Napthyl |
| 1227 | Ph | Me | 2-Napthyl |

According to a further preferred embodiment, the present invention provides a compound of formula (5)

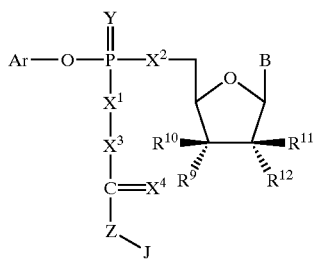
(5)

wherein Ar, Y, $X^1$, $X^2$, $X^3$, $X^4$, Z, J, $R^9$, $R^{10}$, $R^{11}$, $R^{12}$, Q and B as defined above.

More preferably, the invention provides a compound, according to formula (5), of the formula (6):

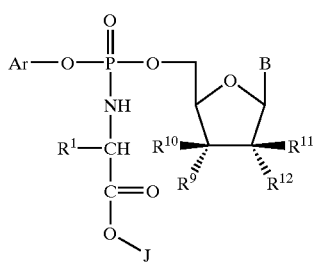
(6)

wherein Ar, $R^1$, J, $R^9$, $R^{10}$, $R^{11}$, $R^{12}$, and B are as defined above.

According further preferred embodiment, the present invention provides a compound of formula (7):

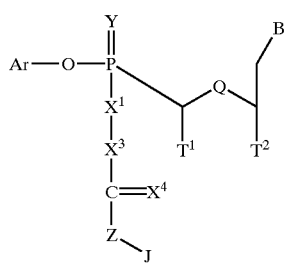
(7)

wherein Ar, Y, $X^1$, $X^3$, $X^4$, Z, J, Q and B are as defined above and $T^1$ and $T^2$ are independently selected from H and $CH_2R^8$ wherein $R^8$ is as defined above. Preferably, B is a purine base. More preferably, B is adenine. Preferably, $T^1$ is hydrogen. Preferably, $T^2$ is $CH_2R^8$. These compounds are analogues of the acyclic nucleoside analogue 9-(2-phosphonylmethoxyethyl) adenine (PMEA), which has been demonstrated to show activity against herpes viruses and retroviruses (Calio et al., Antiviral Res., (1994), 23(1), 77–89; Balzarini et al., AIDS, (1991), 5(1), 21–28).

More preferably, the invention provides a compound, according to formula (7), of formula (8):

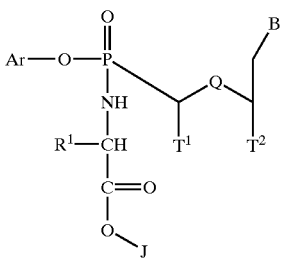
(8)

wherein Ar, $R^1$, J, $T^1$, $T^2$ and B are as defined above.

It is a feature of the aryl ester phosphate compounds (1) of the present invention that they exhibit significantly enhanced anti-viral efficacy, in both in vitro and in vivo tests, in comparison to their corresponding nucleoside analogue (9)

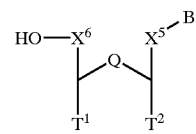
(9)

In addition, the compounds of the present invention exhibit significantly reduced toxicity in comparison to their corresponding analogue (9).

The compounds of the present invention thus exhibit a greatly enhanced selectivity index (ratio of $CC_{50}$ (toxicity): $EC_{50}$ (activity)) in comparison to their corresponding nucleoside analogue.

Experiments with radiolabelled compounds of the present invention have shown that the compounds give enhanced intracellular levels of nucleoside 5'-triphosphate, the enhancement being particularly significant in TK⁻ cells. Thus, the compounds of the present invention may act in part by the known metabolic pathway.

However, it has been found that the compounds of the present invention show surprising activity against nucleoside resistant strains of HIV. This indicates that the compounds of the present invention are also acting by a pathway independent of a 5'-triphosphate metabolite.

It has been demonstrated that the compounds of the present invention lead to intracellular generation of high levels of a metabolite (10).

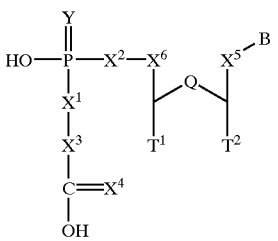
(10)

Metabolite (10) may also be prepared by treatment of the corresponding compound according to formula (1) with hog liver esterase. Moreover, it has been shown that compounds of formula (10) are direct inhibitors of reverse transcriptase from HIV.

According to a further aspect of the present invention there is provided a compound of formula (10)

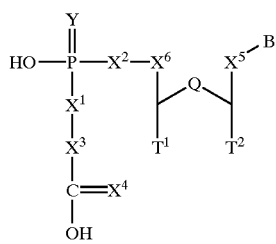

(10)

wherein Ar, Y, $X^1$, $X^2$, $X^3$, $X^4$, $X^6$, $T^1$, $T^2$, Q, $X^5$ and B are as defined above, or a pharmaceutically acceptable derivative or metabolite thereof.

The intracellular generation of anti-viral metabolites such as (10) is an important feature of the invention for several reasons. Firstly, the direct activity of (10) on RT removes the necessity for further nucleotide-kinase mediated phosphorylation, which may be slow in many cases. In cases where the nucleoside monophosphate is not a substrate for host nucleotide kinases, activation will be poor and antiviral efficacy low, even if the triphosphate is an excellent RT inhibitor. In such cases, the generation of metabolites such as (10) may lead to a very significant enhancement in antiviral action. Such compounds may be acting directly in their own right or via a rearrangement, decomposition or disproportionation product or via a contaminant. Moreover, the structure of metabolites such as (10) may be further designed to optimise binding to the known structure of RT, and such modified metabolites could be delivered intracellularly using technology herein described, to further enhance the anti-viral effect.

By "a pharmaceutically acceptable derivative" is meant any pharmaceutically acceptable salt, ester or salt of such ester or any other compound which upon administration to a recipient is capable of providing (directly or indirectly) a compound of formula (1) or (10). By "pharmaceutically acceptable metabolite" is meant a metabolite or residue of a compound of formula (1) or (10) which gives rise to a nucleoside-resistance independent or nucleoside 5'-triphosphate independent mode of reverse transcriptase inhibition exhibited by the compounds of formula (1) or (10).

According to a further aspect of the present invention there is provided a compound according to the present invention for use in a method of treatment, preferably in the prophylaxis or treatment of viral infection.

According to a further aspect of the present invention there is provided use of a compound according to the present invention in the manufacture of a medicament for the prophylaxis or treatment of viral infection.

According to a further aspect of the present invention there is provided a method of prophylaxis or treatment of viral infection comprising administration to a patient in need of such treatment an effective dose of a compound according to the present invention.

The viral infection may comprise any viral infection such as HIV and herpes virus, including HSV 1 and HSV 2, CMV, VZV, EBV, HAV, HBV, HCV, HDV, papilloma, rabies and influenza.

Preferably, the viral infection comprises HIV infection, more preferably HIV-I or HIV-II. It is a feature of the present invention that the compounds exhibit good activity against both HIV-I and HIV-II.

According to a further aspect of the present invention there is provided use of a compound of the present invention in the manufacture of a medicament for use in the inhibition of a reverse transcriptase by a nucleoside-resistance independent or nucleoside 5'-triphosphate independent mode of action.

According to a further aspect of the present invention there is provided a pharmaceutical composition comprising a compound of the present invention in combination with a pharmaceutically acceptable excipient.

According to a further aspect of the present invention there is provided a method of preparing a pharmaceutical composition comprising the step of continuing a compound of of the present invention with a pharmaceutically acceptable excipient.

The medicaments employed in the present invention can be administered by oral or parenteral routes, including intravenous, intramuscular, intraperitoneal, subcutaneous, transdermal, airway (aerosol), rectal, vaginal and topical (including buccal and sublingual) administration.

For oral administration, the compounds of the invention will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In general a suitable dose will be in the range of 0.1 to 300 mg per kilogram body weight-of the recipient per day, preferably in the range of 6 to 150 mg per kilogram body weight per day and most preferably in the range 15 to 100 mg per kilogram body weight per day. The desired dose is preferably presented as two, three, four, five or six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

According to a further aspect of the present invention there is provided a process for the preparation of a compound according to the present invention, the process comprising reaction of a compound of formula (11)

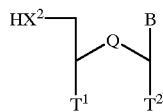

with a compound formula (12)

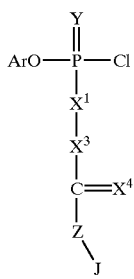

The reaction may be carried out in the tetrahydrofuran in the presence of N-methylimidazole.

Alternatively, the compounds of the present invention may be prepared by reaction of a compound of formula (13) or a suitable derivative thereof

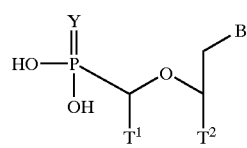

with ArOH and a compound of formula (14) or suitable derivatives thereof

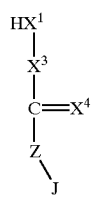

The invention will now be described with reference to the following Figures and Examples. It will be appreciated that what follows is by way of example only and that modifications to detail may be made whilst still falling within the scope of the invention.

FIG. 1 illustrates the in vivo antiviral activity of d4T (comparative) and aryl ester phosphoramidate compound 324 in MSV infected mice. Drug doses are 50[low] or 200[high] mg/kg/day given i.p. for 4 days starting 1 hour before MSV inoculation.

EXPERIMENTAL

All experiments involving water sensitive compounds were conducted under scrupulously dry conditions. Tetrahydofuran was dried by heating under reflux over sodium and benzophenone followed by distallation and storage over active sieves. N-methylimidazole was purified by distillation. Nucleosides were dried at elevated temperature in vacuo over $P_2O_5$. Proton, carbon and phosphorus Nuclear Magnetic Resonance ($^1$H, $^{13}$C, $^{31}$P nmr) spectra were recorded on a Bruker Avance DPX spectrometer operating at 300 MHz, 75.5 MHz, and 121.5 MHz respectively.

All nmr spectra were recorded in $CDCl_3$ at room temperature (20° C. +/−3° C.). $^1$H and $^{13}$C chemical shifts are quoted in parts per million downfield from tetramethyisilane. J values refer to coupling constants and signal splitting patterns are described as singlet (s), broad singlet (bs), doublet (d), triplet (t), quartet (q), multiplet (m) or combinations thereof. $^{31}$P chemical shifts are quoted in parts per million relative to an external phosphoric acid standard. Many NMR peaks were further split due to the presence of diastereoisomers at the [chiral] phosphate centre. Chromatography refers to flash column chromatography and was carried out using Merck silica gel 60H (40–60 m, 230–400 mesh) as stationary phase. Thin layer chromatography was performed using Alugram SIL G/UV$_{254}$ aluminium backed silica gel plates.

Mass spectra were recorded by the fast atom bombardment (FAB) mode on a VG 70–250 spectrometer. HPLC data was recorded using an ACS quaternary system with an ODS5 column and an eluent of water/acetonitrile, with 82% water 0–10 mm, and then a linear gradient to 20% water at 30 min, with a flow rate of 2mL/min and detection by UV at 265 nm.

The test compounds were isolated as mixtures of diastereoisomers, with this isomerism arising from mixed stereochemistry at the phosphate centre. The resulting oils did not give useful microanalytical data but were found to be pure by high-field multinuclear NMR spectroscopy and rigorous HPLC analysis.

Preparation of Compounds

The compounds of the present invention were prepared according to the following general procedures.

Preparation of Aryl Phosphorodichloridates
(General Procedure)

A solution of the appropriate phenol (30.4 mmol) and triethylamine (4.25 ml, 30.5 mmol) in dry $CH_2Cl_2$ (25 ml) was added to a solution of freshly distilled $POCl_3$ (10 ml, 107 mmol) in $CH_2Cl_2$ (30 ml) at −50° and the mixture allowed to stir at ambient temperature overnight. The reaction mixture was filtered and the filtrate evaporated. Ether (20 ml) was added and precipitate filtered again. After evaporation the residue was distilled if possible.

Phenyl Methoxyl Alaninyl Phosphorochloridate

A solution of triethylamine (1 ml–7.17 mmol) in 15 ml of dry $CH_2Cl_2$ was added dropwise to a mixture of phenyl phosphorodichloridate (757.4 mg, 3.59 mmol) and L-alanine methyl ester hydrochloride (500 mg, 3.58 mmol) in 50 ml of dry $CH_2Cl_2$ at −80° C. in one hour. The mixture was then stirred vigorously at −50° C. during five hours and $CH_2Cl_2$ evaporated. 25 ml of dry ether was added and precipitate filtered off under nitrogen. Evaporation of ether gave a colourless oil which was used without further purification for the next step.

Preparation of Aryl Phosphates of Nucleoside
Analogues (General Procedure)

Phenyl Methoxyl alaninyl phosphorochoridate (250 mg, 0.9 mmol, 2.0 equivs) was added to a stirred solution of nucleoside analogue 0.45 mmol) and N-methyl imidazole (0.37 ml, 143.5 μl, 1.8 mmol, 4 equivs) in THF (2 ml). After 4 hours, the solvent was removed under reduced pressure. The gum was dissolved in chloroform (10 ml), and washed with 1M HCl (8 ml), sodium bicarbonate (10 ml) and water (15 ml). The organic phase was dried, and the solvent removed in vacuo. The residue was purified by column chromatography on silica with elution by chloroform-methanol (97:3). Pooling and evaporation of the eluent gave the product as a white solid.

Spectral Data

323—2',3'-Dideoxy-2',3'-didehydrothymidine 5'-(p-ethylphenylmethoxyalaninyl)phosphoramidate Yield=79%; $^{31}P$ (CDCl$_3$): 43 ppm; $^1H$ (CDCl$_3$): 9.25 (0.5H, s, B, NH), 9.23 (0.5H, s, A, NH), 7.34 (0.5H, s, H-6, B), 7.33 (0.5H, s, H-6, A), 7.14–7.00 (5H, m, Ph, H-1'), 6.28 (1H, mn, H-3'), 5.88 (1H, m, H-2'), 5.00 (1H, m, H-4'), 4.38–4.25 (2H, m, H-5'), 3.93 (2H, m, ala-NH, ala-CH), 3.70 (1.5H, s, OMe, A), 3.67 (1.5H, s, OMe, B), 2.60 (2H, q, CH$_2$CH$_3$, J=7.5 Hz), 1.84 (1.5H, d, 5-CH$_3$, J=1.2 Hz), 1.80 (1.5H, d, 5-CH$_3$, J=1.2 Hz), 1.31 (3H, m, CH$_2$CH$_3$), 1.19 (3H, m, ala-CH$_3$). $^{13}C$ (CDCl$_3$): 174.25 (ala-CO, A), 174.12 (ala-CO, B), 164.22 (C-4, B), 164.17 (C-4, A), 151.15 (C-2, B), 151.12 (C-2, A), 148.29 (i-Ph, B), 148.16 (i-Ph, A), 141.24 (p-Ph, A), 141.19 (p-Ph, B), 136.06 (C-6, B), 135.76 (C-6, A), 133.50 (C-3', A), 133.15 (C-3', B), 129.11 (o-Ph, A), 129.05 (o-Ph, B), 127.54 (C-2', A), 127.36 (C-2', B), 120.08 (d, m-Ph, B, J=3.9 Hz), 119.90 (d, m-Ph, A, J=4.9 Hz), 111.51 (C-5, A), 111.40 (C-5, B), 89.83 (C-1', B), 89.60 (C-1', A), 84.88 (d, C-4', B, J=8.8 Hz), 84.70 (d, C-4', A, J=8.8 Hz), 67.11 (d, C-5', A, J=4.9 Hz), 66.48 (d, C-5', B, J=4.9 Hz), 52.65 (OMe), 50.26 (ala-CH, B), 50.13 (ala-CH, A), 28.19 (Ph—CH$_2$), 20.97 (d, ala-CH$_3$, B, J=4.9 Hz), 20.90 (d, ala-CH$_3$, A, J=4.9 Hz), 15.69 (Ph—CH$_2$CH$_3$), 12.45 (5-CH$_3$, A), 12.41 (5-CH$_3$, B). MS: C$_{22}$H$_{29}$N$_3$O$_8$P: 494 (MH$^+$, 5), 368 (MH$^+$-thymine, 25), 228 (15), 81 (C$_5$H$_5$O, base peak) Accurate mass: expected 494.1692; found 494.1693; HPLC: RT=27.23 and 27.48 min.

324—2',3'-Dideoxy-2',3'-didehydrothymidine 5'-(phenyl methoxyalaninyl)phohosphoramidate Yield=88%; $^{31}P$(CDCl$_3$): 3.20 and 3.86 ppm; $^1H$(CDCl$_3$): 1.32 and 1.34 (d, 3H, J=6.8 Hz, CH$_3$ ala); 1.81 and 1.84 (d, 3H, 5CH$_3$); 3.69 and 3.70 (s, 3H, OMe); 3.84–4.00 (m, 2H, CH ala+NH ala); 4.32 (m, 2H, H5'); 5.02 (m, 1H, H4'); 5.88 (m, 1H, H2'); 6.33 (m, 1H, H3'); 7.03 (m, 1H, H1'); 7.15–7.35 (m, 6H, Ar+H6); 9.22 and 9.26 (bs, 1H, NH); $^{13}C$ (CDCl$_3$): 12.52 (5CH$_3$); 21.02 (CH$_3$ ala); 50.22–50.35 (CH ala); 52.74 (OMe); 66.62–67.29 (C5'); 84.80–84.88 (C4'); 89.69–89.93 (C1'); 111.44–111.57 (C5); 120.13–120.31 (Ar ortho); 125.30 (Ar para); 127.49–127.65 (C2'); 129.87–129.93 (Ar meta); 133.19–133.50 (C3'); 135.77–136.06 (C6); 150.51 (Ar ipso); 151.16 (C2); 164.14 (C4); 174.12 (CO ala) MS: 466 (MH$^{+o}$,7); 340 (MH$^{+o}$-base); 200 (17); 136 (47); 89 (25); 81 (C$_5$H$_5$O, base peak); HPLC: RT=22.48 and 22.87 min.

327—2',3'-Dideoxy-2',3'-didehydrothymidine 5'-(p-fluorophenylmethoxyalaninyl)phosphoramidate Yield=89% $^{31}P$ (CDCl$_3$): 3.16 ppm; $^1H$ (CDCl$_3$): 9.75 (1H, s, NH), 7.24 (0.5H, d, H-6, B, J=1.2 Hz), 7.17 (0.5H, d, H-6, A, J=1.2 Hz), 7.09 (5H, m, Ph, H-1'), 6.22 (1H, m, H-3'), 5.82 (1H, m, H-2'), 4.94 (1H, m, H-4'), 4.30–3.84 (4H, m, ala-NH, ala-CH, H-5'), 3.63 (1.5H, s, OMe, A), 3.62 (1.5H, s, OMe, B), 1.77 (1.5H, d, 5-CH$_3$, B, J=1.0 Hz), 1.74 (1.5H, d, 5-CH$_3$, A, J=1.0 Hz), 1.29 (1.5H, d, ala-CH$_3$, B, J=7.0 Hz), 1.23 (1.5H, d, ala-CH$_3$, A, J=7.0 Hz). $^{13}C$ (CDCl$_3$): 174.19 (d, ala-CO, B, J=6.8 Hz), 174.00 (d, ala-CO, A, J=6.8 Hz), 164.25 (C-4, B), 164.20 (C-4, A), 159.77 (d, p-Ph, J=243.6 Hz), 151.14 (C-2), 146.25 (i-Ph), 135.99 (C-6, A), 135.70 (C-6, B), 133.40. (C-3', A), 133.05 (C-3', B), 127.61 (C-2', B), 127.45 (C-2', A), 121.70 (m, o-Ph), 116.37 (d, m-Ph, A, J=23.5 Hz), 116.34 (d, m-Ph, B, J=23.5 Hz), 111.45 (C-5, A), 111.32 (C-5, B), 89.87 (C-1', A), 89.63 (C-1', B), 84.66 (d, C-4', J=5.9 Hz), 67.29 (d, C-5', A, J=4.9 Hz), 66.10 (d, C-5', B, J=4.9 Hz), 52.70 (OMe), 50.26 (ala-CH, A), 50.13 (ala-CH, B), 20.92 (d, ala-CH$_3$, A, J=4.8 Hz), 20.88 (d, ala-CH$_3$, B, J=4.8 Hz), 12.45 (5-CH$_3$, B), 12.41 (5-CH$_3$, A). MS: C$_{20}$H$_{24}$N$_3$O$_8$PF: 484 (MH+, 11), 358 (MH$^+$-thymine, 20), 218 (13), 154 (32), 136 (28), 81 (C$_5$H$_5$O, base peak). Accurate mass: expected 484.1285; found 484.1318; HPLC: RT=25.17 and 25.40 min.

526—2',3'-Dideoxy-2',3'-didehydrothymidine 5'-(m-trifluromethylphenylmethoxyalaninyl)phosphoramidate Yield=80% $^{31}P$(CDCl$_3$): 2.49 and 3.16 ppm; $^1H$(CDCl$_3$): 9.06 (1H, s, NH), 7.45 (5H, m, H-6, Ph), 7.03 (1H, m, H-1'), 6.31 (1H, m, H-3'), 5.92 (1H, m, H-2'), 5.03 (1H, m, H-4'), 4.32 (2H, m, H-5'), 3.97 (2H, m, ala-NH, ala-CH), 3.71 (1.5H, s, OMe, B), 3.70 (1.5H, s, OMe, A), 1.86 (1.5H, s, 5-CH$_3$, B), 1.80 (1.5H, d, 5-CH$_3$, A), 1.36 (3H, m, ala-CH$_3$). $^{13}C$ (CDCl$_3$): 174.06 (d, ala-CO, A, J=6.8 Hz), 173.89 (d, ala-CO, B, J=6.8 Hz), 163.91 (C-4, A), 163.86 (C-4, B), 150.96 (C-2), 150.71 (d, a-Ph, J=5.9 Hz), 135.86 (C-6, A), 135.66 (C-6, B), 133.30 (C-3', A), 133.02 (C-3', B), 132.00 (q, c-Ph, J=32.0 Hz), 130.66 (e-Ph), 127.34 (C-2', B), 127.74 (C-2', A), 123.98 (f-Ph, A), 123.84 (q, CF$_3$, J=272.0 Hz), 123.79 (f-Ph, B), 122.14 (d-Ph), 117.54 (d, b-Ph, J=3.9 Hz), 111.61 (C-5, B), 111.44 (C-5, A), 90.04 (C-1', B), 89.77 (C-1', A), 84.61 (d, C-4', J=7.8 Hz), 67.60 (d, C-5', B, J=4.9 Hz), 66.89 (d, C-5', A, J=4.9 Hz), 52.87 (OMe), 50.32 (d, ala-CH, A, J=4.8 Hz), 50.26 (d, ala-CH, B, J=4.8 Hz), 21.11 (d, ala-CH$_3$, B, J=4.9 Hz), 20.99 (d, ala-CH$_3$, A, J=4.9 Hz), 12.55 (5-CH$_3$, B), 12.47 (5-CH$_3$, A). MS: C$_{21}$H$_{24}$N$_3$O$_8$PF$_3$: 534 (MH$^+$, 6), 408 (MH$^+$-thymine, 8), 268 (10), 149 (10), 81 (C$_5$H$_5$O, base peak). Accurate mass: expected 534.1253; found 534.1201; HPLC: RT=30.56 min.

546—2',3'-Dideoxy-2',3'-didehydrothymidine 5'-(3,5-dichlorophenylmethoxyalaninyl)phosphoramidate Yield=70%; $^{31}P$ (CDCl$_3$): 2.83 and 3.42 ppm; $^1H$ (CDCl$_3$): 9.74 (1H, s, NH, 7.40 (1H, s, H-6), 7.29 (3H, m, Ph), 7.14 (1H, mn, H-1'), 6.44 (1H, m, H-3'), 6.04 (1H, m, H-2'), 5.14 (5H, m, H-4'), 4.48–4.07 (5H, m, ala-NH, ala-CH, H-5'), 3.84 (3H, s, OMe), 1.97 (1.5H, s, 5-CH$_3$, A), 1.92 (1.5H, s, 5-CH$_3$, B), 1.48 (3H, m, ala-CH$_3$). $^{13}C$ (CDCl$_3$): 173.93 (ala-CO), 164.09 (C-4), 151.27 (i-Ph), 151.06 (C-2), 136.01 (m-Ph), 135.60 (C-6), 133.14 (C-3', B), 132.89 (C-3', A), 127.83 (C-2'), 125.69 (p-Ph), 119.40 (o-Ph), 111.54 (C-5, A), 111.40 (C-5, B), 90.03 (C-1', A), 89.74 (C-1', B), 84.60 (C-4'), 67.68 (C-5', A), 66.98 (C-5', B), 52.85 (OMe), 50.26 (ala-CH), 20–93 (ala-CH$_3$), 12.51 (5-CH$_3$). MS: C$_{20}$H$_{23}$N$_3$O$_8$PCl$_2$: 534 (MH$^+$, 8), 408 (MH$^+$-thymine, 12), 391 (10), 149 (12), 127 (thymineH+, 12), 81 (C$_5$H$_5$O, base peak). Accurate mass: expected 534.0600; found 534.0589; HPLC RT=32.19 min.

730—2',3'-Dideoxy-2',3'-didehydrothymidine-5'-(phenyl benzyloxyalaninyl)phosphoramidate Yield=92%; $^{31}P$ (CDCl$_3$): 3.40 and 4.04 ppm; $^1H$ (CDCl$_3$): 1.24 and 1.26 (d, 3H, J=6.8 Hz, CH$_3$ ala); 1.70 and 1.74 (s, 3H, 5CH$_3$); 3.86–4.28 (m, 4H, H5'+CH ala+NH); 4.85 (m, 1H, H4'); 5.04 and 5.06 (s, 2H, CH$_2$Ph); 5.74 (d, 1H, H2'); 6.16 (dd, 1H, H3'); 6.90 (m, 1H, H1'); 7.00–7.30 (m, 11H, Ar+H6); 9.61 (d, 1H, NH); $^{13}C$ (CDCl$_3$): 12.52 (5CH$_3$); 20.98 (CH$_3$ ala); 50.36–50.52(CH ala); 66.70–67.18 (C5'); 67.46 (CH$_2$Ph); 84.63–84.76–84.88 (C4'); 89.68–89.88 (C1'); 111.44–111.55 (C5); 120.18–120.25–120.36–120.43 (Ar ortho, OPh); 125.31 (Ar para, OPh); 127.48–127.61 (C2'); 128.45–128.79–128.83 (Ar, CH$_2$Ph); 129.87–129.93 (Ar meta, OPh); 133.16–133.45 (C3'); 135.35 (Ar1, CH$_2$Ph); 135.79–136.07 (C6); 150.44 (Ar1, OPh); 151.18 (C2); 164.21–164.28 (C4); 173.42–173.51–173.65 (CO ala); HPLC: RT=34.96 and 35.07 min; MS: C$_{26}$H$_{28}$O$_8$N$_3$P: 542(MH$^{+\circ}$; 17); 416 (MH$^{+\circ}$_base; 40); 81(100). Accurate mass: expected 542.1716; found 542.1712.

776—2',3'-Dideoxy-2',3'-didehydrothymidine-5'-(2,4-dibromophenylmethoxyalaninyl)phosphoramidate Yield=88%; $^{31}$P (CDCl$_3$): 3.07 and 3.62 ppm; $^1$H (CDCl$_3$): 1.26 and 1.28 (d, 3H, J=6.8 Hz, CH$_3$ ala); 1.75 and 1.80 (s, 3H, 5CH$_3$); 2.11 (s, 1H, NH); 3.64 (s, 3H, OMe); 3.92–4.30 (m, 3H, H5'+CHala); 4.98 (m, 1H, H4'); 5.87 (m, 1H, H2'); 6.26 (m, 1H, H3'); 6.96 (m, 1H, H1'); 7.30–7.60 (m, 4H, Ar+H6); 9.41(bs, 1H, NH). $^{13}$C (CDCl$_3$): 12.51 (5CH$_3$); 21.00 (CH$_3$ ala); 50–24 (CHala); 52.80 (OMe); 67.37–67.83 (C5'); 84.49–84.61 (C4'); 89.80–89.92 (C1'); 111.60 (C5); 115.49 (Ar2); 118.26 (Ar4); 122.61–122.89 (Ar6); 127.70 (C2'); 131.86 (Ar5); 133.06–133.21 (C3'); 135.64 (Ar3); 135.75–135.88 (C6); 147.01 (Ar1); 151.07 (C2); 164.03 (C4); 173.71–173.82 (COala); HPLC: RT=41.17 and 41.30 min; MS: C$_{20}$H$_{22}$O$_8$N$_3$PBr$_2$: 622, 624, 626 (MHz$^{+\circ}$; 3, 6, 3); 496, 498, 500 (MH$^{+\circ-}$base; 5, 9, 5); 81 (100). Accurate mass: expected 621.9516; found 621.9507.

779—2',3'-Dideoxy-2,3'-didehydrothymidine-5'-(2,3,4,5,6-pentafluorophenylmethyoxyalaninyl)phosphoramidate Yield=76%; $^{31}$P (CDCl$_3$): 4.74 and 5.66 ppm; $^1$H (CDCl$_3$): 1.34 and 1.36 (d, 3H, J=6.7 Hz, CH$_3$ ala); 1.75 and 1.81 (s, 3H, 5CH$_3$); 3.69 (s, 3H, OMe); 3.92–4.40 (m, 4H, H5'+CH ala+NH); 4.97 (m, 1H, H4'); 5.85 (m, 1H, H2'); 6.29 (m, 1H, H3'); 6.93 (m, 1H, H1'); 7.19 (m, 1H, H6); 9.38 (bs, 1H, NH). $^{13}$C (CDCl$_3$): 12.23–12.43 (5CH$_3$); 20.83 (CH$_3$ ala); 50.22–50.34 (CH ala); 52.99 (OMe); 67.75–68.37 (C5'); 84.42–84.52 (C4'); 89.87–90.17 (C1'); 111.75 (C5); 127.69–127.93 (C2'); 132.86–133.13 (C3'); 132–143 (m, Ar); 135.74–135.96 (C6); 151.11 (C2); 164.15 (C4); 173.64–173.76 (COala); Mass (NOBA matrix): C$_{20}$H$_{19}$O$_8$N$_3$PF$_5$: 556 (MH$^{+\circ}$, 31); 578 (M$^{\circ+}$Na, 100); HPLC: RT=35.90 min.

862—2',3'-Dideoxy-2',3'-didehydrothymidine 5'-(phenyl hexyloxyalaninyl)phosphoramidate Yield=88%; $^{31}$P (CDCl$_3$): 3.99 and 4.60 ppm; $^1$H (CDCl$_3$): 0.94 (m, 3H, C$\underline{H}_3$CH$_2$); 1.28–1.41 (m, 9H, CH$_3$ ala +3×CH$_2$); 1.65 (m, 2H, CO$_2$CH$_2$C$\underline{H}_2$); 1.90 and 1.93 (s, 3H, 5CH$_3$); 4.00–4.20 (m, 4H, CH ala+NH ala+CO$_2$C$\underline{H}_2$); 4.37 (m, 2H, H5'); 5.05 (m, 1H, H4'); 5.94 (m, 1H, H2'); 6.38 (m, 1H, H3'); 7.10 (m, 1H, H1'); 7.15–7.36 (m, 6H, Ar+H6); 9.48 and 9.51 (s, 1H, NH). $^{13}$C (CDCl$_3$): 12.76 (5CH$_3$); 14.39 ($\underline{C}$H$_3$CH$_2$); 21.45 (CH$_3$ ala); 22.88, 25.82, 28.82 and 31.72 (CH$_2$); 50.63 (CH ala); 66.26 (OCH$_2$); 66.89–67.43 (C5'); 85.03 (C4'); 89.97 (C1'); 111.68–111.83 (C5); 120.55 (Ar ortho); 125.57 (Ar para); 127.86 (C2'); 130.15 (Ar meta); 133.47–133.70 (C3'); 136.03–136.31 (C6); 150.72 (Ar ipso); 151.37–151.39 (C2); 164.35–164.42 (C4); 174.02 (CO ala); Mass (NOBA matrix): C$_{25}$H$_{34}$O$_8$N$_3$P: 536 (MH$^{+\circ}$,24); 558 (M$^{\circ+}$Na, 37).

863—2',3'-Dideoxy-2',3'-didehydrothymidine-5'-(phenyl Methoxyphenyl-alaninyl)phosphoramidate Yield=89%; $^{31}$P (CDCl$_3$): 3.96 and 4.35 ppm; $^1$H (CDCl$_3$): 1.89 (s, 3H, 5CH$_3$); 3.00 (m, 2H, CH$_2$Ph); 3.74 (s, 3H, OMe); 3.80–4.28 (m, 4H, CH ala+NH ala+H5'); 4.94 (m, 1H, H4'); 5.91 (m, 1H, H2'); 6.21–6.30 (m, 1H, H3'); 7.04–7.32 (m, 12H, Ar+H1+H6); 9.35 (s, 1H, NH). $^{13}$C (CDCl$_3$): 12.54 (5CH$_3$); 40.55 (CH$_2$Ph); 52.63 (OMe); 55.72–56.01 (CH ala); 66.50–67.10 (C5'); 84.78 (C4'); 89.71–89.95 (C1'); 111.53–111.64 (C5); 120.28 (Ar ortho, OPh); 125.40 (Ar para, OPh); 127.52 (C2'); 128.86, 129.65 and 129.98 (Ar, CH$_2$Ph); 129.86–129.92 (Ar meta, OPh); 133.18–133.50 (C3'); 135.72 (Ar ipso, CH$_2$Ph); 135.79–136.06 (C6); 150.46 (Ar ipso, OPh); 151.13–151.17 (C2); 164.12–164.18 (C4); 173.00 (CO ala); Mass (NOBA matrix): C$_{26}$H$_{28}$O$_8$N$_3$P: 542 (MH$^{+\circ}$, 77); 564 (M$^{\circ+}$Na, 29).

864—2',3'-Dideoxy-2',3'-didehydrothymidine-5'-(phenyl Methoxypheleucinyl)phosphoramidate Yield=87%; $^{31}$P (CDCl$_3$): 4.18 and 4.83 ppm; $^1$H (CDCl$_3$): 0.91 (m, 6H, (C$\underline{H}_3$)$_2$CH); 1.42–1.70 (m, 3H, C$\underline{H}$CH(CH$_3$)$_2$); 1.91 and 1.93 (s, 3H, 5CH$_3$); 3.73 (s, 3H, OMe); 3.76–3.98 (m, 2H, CH ala+NH ala); 4.28–4.46 (m, 2H, H5'); 5.08 (m, 1H, H4'); 5.96 (m, 1H, H2'); 6.36 (m, 1H, H3'); 7.09 (m, 1H, H1'); 7.18–7.35 (m, 6H, Ar+H6); 9.35 (s, 1H, NH). $^{13}$C (CDCl$_3$) 12.76 (5CH$_3$); 22.23–23.01 (($\underline{C}$H$_3$)$_2$CH); 24.75 ($\underline{C}$H(CH$_3$)$_2$); 43.86–44.11 ($\underline{C}$H$_2$CH(CH$_3$)$_2$); 52.75 (OMe); 53.42–53.60 (CH ala); 66.92–67.55 (C5'); 85.62 (C4'); 89.92–90.19 (C1'); 111.69–111.83 (C5); 120.37–120.62 (Ar ortho); 125.55–125.58 (Ar para); 127.79 (C2'); 130.12 (Ar meta); 133.51–133.70 (C3'); 136.00–136.36 (C6); 151.05 (Ar ipso); 151.38 (C2); 164.39–164.50 (C4); 174.55–174.88 (CO ala); Mass (NOBA matrix): C$_{23}$H$_{30}$O$_8$N$_3$P: 508 (MH$^{+\circ}$,62); 530 (M$^{\circ+}$Na, 59).

865—2',3'-Dideoxy-2',3'-didehydrothymidine-5'-(phenyl methoxyvalinyl)phosphoramidate Yield=86%; $^{31}$P (CDCl$_3$): 4.85 and 5.40 ppm; $^1$H (CDCl$_3$): 0.92 (m, 6H, (C$\underline{H}_3$)$_2$CH); 1.82 (m, 3H, C$\underline{H}$(CH$_3$)$_2$); 1.89 and 1.91 (s, 3H, 5CH$_3$); 3.76 (s, 3H, OMe); 3.82 (m, 2H, CH ala+NH ala); 4.30–4.48 (m, 2H, H5'); 5.07 (m, 1H, H4'); 5.96 (m, 1H, H2'); 6.38 m, 1H, H3'); 7.10 (m, 1H, H1'); 7.18–7.35 (m, 6H, Ar+H6); 9.31 (s, 1H, NH). $^{13}$C (CDCl$_3$): 12.80 (5CH$_3$); 17.77–19.24 (($\underline{C}$H$_3$)$_2$CH); 32.43–32.62 ($\underline{C}$H(CH$_3$)$_2$); 52.67 (OMe); 60.32–60.38 (CH ala); 66.92–67.65 (C5'); 85.04 (C4'); 89.98–90.24 (C1'); 111.76–111.87 (C5); 120.45–120.56 (Ar ortho); 125.54–125.59 (Ar para); 127.81–127.86 (C2'); 130.13–130.17 (Ar meta); 133.51–133.72 (C3'); 136.01–136.28 (C6); 150.83 (Ar ipso); 150.87–151.34 (C2); 164.30–164.37 (C4); 173.56–173.65 (CO ala); Mass C$_{22}$H$_{28}$O$_8$N$_3$P: 493.6 (MH$^{+\circ}$,100).

866—2',3'-Dideoxy-2',3'-didehydrothymidine-5'-(phenyl methoxyglycinyl)phosphoramidate Yield=90%; $^{31}$P (CDCl$_3$): 4.89 and 5.52 ppm; $^1$H (CDCl$_3$): 1.79 and 1.83 (s, 3H, 5CH$_3$); 3.69 (s, 3H, OMe); 3.70–4.05 (m, 4H, CH$_2$NH+CH ala+NH ala); 4.32 (m, 2H, H5'); 4.99 (m, 1H, H4'); 5.92 (m, 1H, H2'); 6.38 (m, 1H, H3'); 6.98 (m, 1H, H1'); 7.05–7.38 (m, 6H, Ar+H6); 9.44 and 9.46 (s, 1H, NH). $^{13}$C (CDCl$_3$): 12.75 (5CH$_3$); 43.15 ($\underline{C}$H$_2$NH); 52.94 (OMe); 66.78–67.52 (C5'); 84.98–85.10 (C4'); 89.68–90.16 (C1'); 111.69–111.80 (C5); 120.46–120.59 (Ar ortho); 125.66 (Ar para); 127.66–127.91 (C2'); 130.22 (Ar meta); 133.48–133.87 (C3'); 136.11–136.40 (C6); 150.65 (Ar ipso); 151.45 (C2); 164.46 (C4); 171.41–171.51 (CO ala); Mass (NOBA matrix): C19H$_{22}$O$_8$N$_3$P: 452 (MH$^{+\circ}$,74); 474 (M$^{\circ+}$Na, 46).

867—2',3'-Dideoxy-2',3'-didehydrothymidine-5'-(phenyl methoxymethioninyl)phosphoramidate Yield=81%; $^{31}$P (CDCl$_3$): 4.09 and 4.86 ppm; $^1$H (CDCl$_3$): 1.74 and 1.79 (s, 3H, CH$_3$S); 1.94 and 1.97 (s, 3H, 5CH$_3$); 1.80–2.40 (m, 5H, C$\underline{H}$C$\underline{H}_2$C$\underline{H}_2$S); 3.72 and 3.74 (s, 3H, OMe); 3.98–4.32 (m, 4H, H5'+CH ala+NH ala); 4.96 (m, 1H, H4'); 5.84 (m, 1H, H2'); 6.26 (m, 1H, H3'); 6.96 (m, 1H, H1'); 7.05–7.25 (m, 6H, Ar+H6); 9.58 (bs, 1H, NH); $^3$C (CDCl$_3$) 12.80 (5CH$_3$); 15.68 (CH$_3$S); 29.95 ($\underline{C}$H$_2$SCH$_3$); 33.73–33.85 ($\underline{C}$H$_2$CH$_2$S); 53.06 (OMe); 53.81–54.07 (NH CH); 67.05–67.70 (C5'); 84.90–85.03 (C4'); 89.98–90.23 (C1'); 111.66–111.86 (C5); 120.39–120.66 (Ar ortho); 125.63 (Ar para); 127.81–127.91 (C2'); 130.18 (Ar meta); 133.44–133.69 (C3'); 136.00–136.38 (C6); 150.72–150.80 (Ar ipso); 151.41 (C2); 164.52 (C4); 173.61–173.94 (CO ala); Mass (NOBA matrix): $C_{22}H_{28}O_8N_3PS$: 526 (MH$^{+\circ}$46); 548 (M$^{\circ +}$6Na, 21).

868—2',3'-Dideoxy-2',3'-didehydrothymidine-5'-(2,4-dibromophenylbenzyloxyalaninyl)phosphoramidate Yield=82%; $^{31}P$ (CDCl$_3$): 3.68 and 4.18 ppm; $^1H$ (CDCl$_3$): 1.40 and 1.42 (d, 3H, J=6.7 Hz, CH$_3$ ala); 1.90 and 1.92 (s, 3H, 5CH$_3$); 4.04–4.40 (m, 4H, H5'+CHala+NH ala); 4.98 (m, 1H, H4'); 5.20 (s, 2H, CH$_2$Ph); 5.91 (m, 1H, H2'); 6.27 and 6.35 (m, 1H, H3'); 7.06 (bs, 1H, H1'); 7.30–7.70 (m, 9H, Ar+H6); 9.52 (s, 1H, NH); $^{13}C$ (CDCl$_3$): 12.86 (5CH$_3$); 21.35 (CH$_3$ ala); 50.68–50.76 (CHala); 67.67–68.03 (C5'); 67.88 (CH$_2$Ph); 84.85 (C4'); 90.10–90.20 (C1'); 111.88–111.92 (C5); 115.76–115.91 (Ar2); 118.62–118.72 (Ar4); 122.91–123.22 (Ar6); 127.98 (C2'); 128.75–129.01–129.12 (Ar o,m,p, CH$_2$Ph); 132.20 (Ar5); 133.38–133.51 (C3'); 135.48 (Ar ipso, CH$_2$Ph); 135.96 (Ar3); 136.21 (C6); 147.28 (Ar1); 151.39 (C2); 164.34–164.38 (C4); 173.47–173.62 (COala); Mass (NOBA matrix): $C_{26}H_{26}O_8N_3PBr_2$: 699–700–701 (MH$^{-\circ}$, 27-49-29); 721–722–723 (M$^{\circ +}$Na, 17-21-17).

877—2',3'-Dideoxy-2,3'-didehydrothymidine-5'-(phenyl methoxyglycinyl)phosphoramidate Yield=83%; $^{31}P$ (CDCl$_3$): 3.91 and 4.33 ppm; $^1H$ (CDCl$_3$): 1.83 and 1.85 (s, 3H, 5CH$_3$); 3.01 (m, 2H, CHCH$_2$Ph); 3.78–4.30 (m, 4H, H5'+HNCH); 4.92 (m, 1H, H4'); 5.89 (m, 1H, H2'); 6.18 and 6.27 (m, 1H, H3'); 7.00–7.40 (m, 17H, Ar+H1'+H6); 9.35 (bs, 1H, NH); $^{13}C$ (CDCl$_3$): 12.62–12.75 (5CH$_3$); 40.65–40.73 (CHCH$_2$Ph); 55.95–56.26 (NHCH); 66.79–67.27 (C5'); 67.80 (CH$_2$Ph); 84.87–85.05 (C4'); 89.92–90.14 (C1'); 111.72–111.82 (C5); 120.45–120.52 (Ar ortho, OPh); 125.60 (Ar para, OPh); 127.73 (C2'); 129.01–129.07–129.11–129.91–130.15–130.38–135.29–135.85 (Ar, 2×CH$_2$Ph); 130.21 (Ar meta, OPh); 133.36–133.63 (C3'); 136.24 (C6); 150.68–150.77 (Ar ipso, OPh); 151.31–151.35 (C2); 164.28–164.34 (C4); 172.48–172.64 (CO ala); Mass (NOBA matrix): $C_{32}H_{32}O_8N_3P$: 618 (MH$^{+\circ}$, 78); 640 (M$^{\circ +}$Na, 52).

878—2°,3'-Dideoxy-2',3'-didehydrothymidine-5'-(phenyl tert-butoxyphenylalaninyl)phosphoramidate Yield=79%; $^{31}P$ (CDCl$_3$): 4.27 and 4.50 ppm; $^1H$ (CDCl$_3$): 1.40 and 1.41 (s, 9H, tBu); 1.84 and 1.87 (s, 3H, 5CH$_3$); 3.00 (m, 2H, CH$_2$Ph); 3.76–4.28 (m, 4H, H5'+HNCH); 4.95 (m, 1H, H4'); 5.86 and 5.91 (m, 1H, H2'); 6.26 and 6.30 (m, 1H, H3'); 7.04 (m, 1H, H1'); 7.12–7.25 (m, 11H, Ar+H6); 9.38 and 9.40 (bs, 1H, NH); $^{13}C$ (CDCl$_3$): 12.76–12.79 (5CH$_3$); 28.31 ((CH$_3$)$_3$C); 40.96–41.04 (CH$_2$Ph); 56.31–56.65 (NHCH); 66.79–67.28 (C5'); 82.90–82.92 ((CH$_3$)$_3$C); 84.94–85.03 (C4'); 89.93–90.11 (C1'); 111.67–111.86 (C5); 120.45 (Ar ortho, OPh); 125–52 (Ar para, OPh); 127.77 (C2'); 127.88–128.83–128.92–136.02 (Ar, CH$_{2Ph}$); 130.13 (Ar meta, OPh); 133.54–133.60 (C3'); 136.31 (C6); 150.75–150.84 (Ar ipso, OPh); 151.36 (C2); 164.32–164.37 (C4); 171.89 (CO ala); Mass (NOBA matrix): $C_{29}H_{34}O_8N_3P$: 584 (MH$^{+\circ}$, 26); 606 (M$^{\circ +}$Na, 41).

892—2',3'-Dideoxy-2',3'-didehydrothymidine 5'-(phenyl cyclohexyloxyalaninyl)phosphoramidate Yield=83%; $^{31}P$ (CDCl$_3$) 4.11 and 4.71 ppm. $^1H$ (CDCl$_3$) 1.08–1.82 (m, 16H, CH$_3$ ala+5CH$_3$+cyclohexyl); 3.79–4.14 (m, 2H, CH ala+NH ala); 4.27 (m, 2H, H5'); 4.69 (m, CH cyclohexyl); 4.96 (m, 1H, H4'); 5.80 (m, 1H, H2'); 6.24 (m, 1H, H3'); 6.98 (m, 1H, H1'); 7.04–7.32 (m, 6H, Ar+H6); 9.66 and 9.82 (bs, 1H, NH). $^{13}C$ (CDCl$_3$) 12.58 (5CH$_3$); 21.18–21.32 (CH$_3$ ala); 23.73–25.40–31.49–31.58(CH$_2$ cyclohexyl); 50.47–50.61 (CH ala); 66.69–67.24 (C5'); 74.36 (CH cyclohexyl); 84.87 (C4'); 89.72–89.92 (C1'); 111.48–111.63 (C5); 120.26–120.49 (Ar ortho); 125.32–125.37 (Ar para); 127.59–127.73 (C2'); 129.91–129.98 (Ar meta); 133.30–133.51 (C3'); 135.89–136.16 (C6); 150.53 (Ar ipso); 150.67–151.31 (C2); 164.36–164.41 (C4); 173.23 (CO ala); Mass (NOBA matrix): $C_{25}H_{32}O_8N_3P$: 534 (MH$^{+\circ}$, 56); 556 (M$^{\circ +}$Na, 42).

893—2',3'-Dideoxy-2',3'-didehydrothymidine 5'-(phenyl tert-utyloxyalaninyl)phosphoramidate Yield=79%; $^{31}P$ (CDCl$_3$): 4.17 and 4.67 ppm. $^1H$ (CDCl$_3$): 1.34 (m, 3H, CH$_3$ ala); 1.46 (m, 9H, CH$_3$ tBu); 1.87 (d, 3H, 5CH$_3$); 3.82–4.06 (m, 2H, H5'); 4.29–4.49 (m, 2H, CH ala+NH ala); 5.05 (m, 1H, H4'); 5.91 (m, 1H, H2'); 6.35 (m, 1H, H3'); 7.06 (m, 1H, H1'); 7.15–7.40 (m, 6H, Ar+H6); 9.60 (bs, 1H, NH). $^{13}C$ (CDCl$_3$): 12.54 (5CH$_3$); 21.19–21.35 (CH$_3$ ala); 28.07 (C(CH$_3$)$_3$); 50.80–50.89 (CH ala); 66.60–67.18 (C5'); 82.41–82.45(C(Me)$_3$); 84.82 (C4'); 89.67–89.87 (C1'); 111.44–111.60 (C5); 120.22–120.41 (Ar ortho); 125.28–125.31 (Ar para); 127.54–127.65 (C2'); 129.88–129.94 (Ar meta); 133.33–133.47 (C3'); 135.84–136.10 (C6); 150.51 (Ar ipso); 150.65–151.20 (C4); 164.19–164.23 (C2); 172.78–172.93 (CO ala); Mass (NOBA matrix): $C_{23}H_{30}O_8N3P$: 508 (MH$^{+\circ}$, 82); 530 (M$^{\circ +}$Na, 48).

2',3'-Dideoxy-2',3'-didehydrothymidine-5'-(phenylmethoxy-B-alaninyl)phosphateCf1197

Yield=64%; $^{31}P$ (CDCl$_3$): 6.44, 6.70(1:3); $^1H$ (CDCl$_3$): 1.87° (s, 3H, 5-CH$_3$), 2.42(t, 2H, CH$_2$ ala), 3.22° (m, 2H, CH$_2$ ala), 3.62 (s, 3H, OCH$_3$), 4.09 (m, 1H, H4'), 4.18–4.39 (m, 2H, H5'), 4.97 (bs, 1H, NH ala), 5.88° (m, 1H, H2'), 6.32 (m, 1H, H3'), 6.99 (m, 1H, H1'), 7.08–7.38 (m, 5H, Ph and H6), 10.01 (bs, 1H, base NH); $^{13}C$ (CDCl$_3$): 14.52 (5-CH$_3$), 37.80° (CH, ala), 39.28° (CH$_2$ ala), 53.91° (OCH$_3$), 68.57° (d, J=3.92 Hz, C5'), 86.90 (d, J=8.38 Hz, C4'), 91.68° (C1'), 113.40° (C5), 122.34 (d, J=4.68 Hz, ortho-Ph), 127.23 (C2'), 129.55° (para-Ph), 131.81° (meta-Ph), 135.45° (C6), 137.99° (C3'), 152.60° (d, J=5.96 Hz, ipso-Ph), 153.44 (C2), 166.58 (C4), 174.55° (COO); Mass (NOBA matrix): $C20H_{24}N_3O_8P$ 126 (thymine$^+$,5), 127 (thymineH$^+$,4), 242 ($C_{10}H_{13}PO_4N^+$,9) 243 ($C_{10}H_{14}PO_4N^+$,3), 465 (M$^+$,4), 466 (MH$^+$, 8), 467 (MHNa$^+$, 20), 168 (MHNa$^+$, $^3$O, 5), 187 (MNa$^+$, 3), 188 (MHNa$^+$, 97), 189 (MHNa$^+$, $^{13}C$, 21); High Resolution MS: found 466.1379 (MH$^+$), $C_{20}H_{25}N_3O_8P$ requires 466.1379; HPLC: RT=22.81, 23.27 mins (1:1).

2',3'-Dideoxy-2',3'-didehydrothymidine-5'-(phenyl methoxy-α-aminobutylryl)phosphateCf1198

Yield=65%; $^{31}P$ (CDCl$_3$): 6.11, 6.66 (1:2); $^1H$ (CDCl$_3$): 1.78 (m, 2H, CH$_2$ GABA), 1.85° (s,3H, 5-CH$_3$), 2.35 (t, 2H, J=6.95 Hz, CH$_2$ GABA), 2.97° (m, 2H, CH$_2$ GABA), 3.68 (s, 3H, OCH$_3$), 3.93° (m, 1H, H4'), 4.28° (m, 1H, H5'), 4.35° (m, 1H, H5'), 5.02 (bs, 1H, NH GABA), 5.82° (m, 1H, H2'), 6.31 (m, 1H, H3'), 6.98 (m, 1H, H1'), 7.11–7.37 (m, 6H, Ph and H6), 9.91 (bs, 1H, base NH); $^{13}C$(CDCl$_3$): 12.64 (5-CH$_3$), 26.72° (CH, GABA), 32.25° (CH$_2$ GAEA) 40.98° (CH$_2$ GABA), 51.94 (OCH$_3$), 66.93° (C5'), 85.11 (d, J=8.30 Hz, C4'), 111.40 (C5), 120.46° (d, J=4.83 Hz, ortho-PH), 125.24 (C2'), 127.59° (para-Ph), 129.88° (meta-Ph), 133.68° (C6), 136.28° (C3'), 150.86° (d, J=6.45 Hz, ipso-Ph), 151.61 (C2), 164.80 (C4), 173.86° (COO); Mass (matrix NOBA): $C_{21}H_{26}N_3O_8P$: 127 (thymineH$^+$, 28), 479 (M$^+$, 3), 480 (MH$^+$, 59), 481 (MH$^+$, $^{13}C$, 17), 501 (MNa$^+$, 3), 502 (MHNa$^+$,59), 503 (MHNa$^+$, $^{13}C$, 16); High Resolution MS: found 480.1486 (MH$^+$), $C_{21}H_{22}N_3O_8P$ requires 480.1536; HPLC: RT 23.90, 24.33 mins (1:1).

2',3'-Dideoxy-2',3'-didehydrothymidine-5'-(phenyl methoxy-2-aminoisobutylryl)phosphateCf1200

Yield=36%; $^{31}$P (CDCl$_3$): 2.38, 3.05 (3:1); $^1$H (CDCl$_3$): 1.53° (s, 6H, CMe$_2$), 1.91° (s, 2H, 5-CH$_3$), 3.71 (s, 3H, OCH$_3$), 4.31 (m, 2H, H5'), 4.23–4.41 (m, 3H, H4' and H5'), 5.03 (bs, 1H, P-NH) 5.89° (m, 1H, H2'), 6.28° (m, 1H, H3'), 6.99–7.31 (m, 7H, Ph, HO and H1'), 9.09 (bs, 1H, base NH); $^{13}$C (CDCl$_3$): 14.27 (5-CH$_3$), 28.74° (CMe$_2$), 54.81° (OCH$_3$), 58.88° (CMe$_2$), 69.03° (d, C', J=5.58 Hz), 86.57° (d, J=7.88 Hz, C4'), 91.51° (C1'), 113.24° (C5), 122.01° (d, J=4.95 Hz, ortho-Ph), 126.88 (C2'), 129.25° (para-Ph), 131.57° (meta-Ph), 135.19° (C6), 137.68° (C3'), 152.52° (d, J=3.09 Hz, ortho-Ph), 153.05 (C2), 166.12 (C4), 177.69° (COO); MS (matrix NOBA): 354 ((MH—thymine)$^+$, base peak), 479 (M$^+$, 3), 480 (MH$^+$, 64), 481 (MH$^+$, $^{13}$C, 17), 482 (MH$^+$, 2×$^{13}$C, 3), 502 (MNa$^+$, 92), 503 (MHNa$^+$, 24); High Resolution MS: found 480.1503 (MH$^+$), C$_{21}$H$_{27}$N$_3$O$_8$P requires 480.1536; HPLC: RT 24.79, 25.29 mins (1:1).

2',3'-Dideoxy-2',3'-didehydrothymidine-5'-(phenyl methoxy-6-aminocaproyl)phosphateCf1199

Yield=80%; $^{31}$P (CDCl$_3$): 6.90, 6.30 (1:1); $^1$H (CDCl$_3$): 1.28 (s, 2H, CH$_2$ caproyl), 1.45 (m, 2H, CH$_2$ caproyl), 1.58 (m, 2H, CH$_2$ caproyl), 1.82° (s, 3H, 5-CH$_3$), 2.28 (m, 2H, CH$_2$ caproyl), 2.87 (m, 2H, CH$_2$ caproyl), 3.65 (s, 3H, OCH$_3$), 3.81 (m, 1H, H4'), 4.25 (m, 2H, H5'), 4.95 (bs, 1H, NH caproyl), 5.86° (m, 1H, H2'), 6.31° (m, 1H, H3'), 6.98 (m, 1H H1'), 7.04–7.38° (m, 6H, Ph and H6), 10.12 (bs, 1H, base NH); $^{13}$C (CDCl$_3$): 13.47° (5-CH$_3$), 25.43° (CH$_2$ caproyl), 27.04° (CH$_2$ caproyl), 32.15° (CH$_2$ caproyl), 34.85 (CH$_2$ caproyl), 42.30° (CH$_2$ caproyl), 52.61 (OCH$_3$), 67.92° (C5'), 85.80 (d, J=8.22 Hz), 90.68° (C4'), 112.25° (C5), 121.17° (d, J=4.58 Hz, ortho-Ph), 125.99 (C2'), 128.40° (para-Ph), 130.77 (meta-Ph), 134.38° (C6), 137.09° (C3'), 151.69° (d, J=3.23 Hz, ortho-Ph), 152.26 (C2), 165.36 (C4'), 175.07 (COO); MS (matrix Cl): 127 (thymineH$^+$, 42), 508 (MH, 18), 509 (MH$^{30}$, $^{13}$C, 5); High Resolution MS: found 508.1850 (MH$^+$), C23H$_{31}$N$_3$O$_8$P requires 508.1849; HPLC: RT 26.33 mins.

2',3'-Dideoxy-2',3'-didehydrothymidine-5'-(β-alaninyl) phosphate Ammonium Salt Cf1216

Yield=62%; $^{31}$P (D$_2$O): 8.84; $^1$H (D$_2$O): 1.73 (3H, s, 5-CH$_3$), 2.18 (2H, m, ala CH$_2$), 2.65 (m, 2H, ala CH$_2$), 3.79 (2m, H, H5'), 4.95 (m, 1H, H4'), 5.76 (m, 1H, H2'), 6.35 (m, 1H, H3'), 6.82 (m, 1H, H1'), 7.47 (s, 1H, H6); $^{13}$C (D$_2$O): 11.81 (5-CH$_3$), 38.51 (ala CH$_2$), 39.45 (d, ala CH$_2$, J=6.64 Hz), 65.41 (d, C5', J=4.91 Hz), 86.40 (d, J=9.20 Hz, C4'), 90.20 (C1'), 111.0.7 (C5), 125.40 (C2'), 134.66 (C3'), 138.54 (C6), 152.53 (C2), 167.00 (C4), 181.04 (COO); HPLC: RT=32.74 mins.

2',3'-Dideoxy-2',3'-didehydrothymidine-5'(γ-aminobutylryl) phosphate Ammonium Salt Cf 1224

Yield=54%; $^{31}$P (D$_2$O): 10.03; $^1$H(D$_2$O): 1.47 (m, 2H, GABA CH$_2$), 1.72 (s, 3H, 5-CH$_3$), 1.98 (m, 2H, GABA CH$_2$), 2.48 (m, 2H, GABA CH$_2$), 3.72 (m, 2H, H5'), 4.91 (m, 1H, H4'), 5.72 (m, 1H, H2'), 6.26 (m, 1H, H3'), 6.72 (m, 1H, H1'), 7.45 (s, 1H, H6'). $^{13}$C (D$_2$O): 11.79 (5-CH$_3$), 27.99 (d, J=7.25 Hz, GABA CH$_2$), 34.47 (GABA CH$_2$), 41.17 (GABA CH$_2$), 65.35 (d, J=4.68 Hz, C5'), 86.38 (d, J=9.36 Hz, C4'), 90.27 (C1'), 111.47 (C5), 125.29 (C2'), 134.70 (C3'), 138.68 (C6), 152.47 (C2), 166.95 (C4), 182.32 (COO).

2',3'-Dideoxy-2',3'-didehydrothymidine-5'-(caproyl) phosphate Ammonium Salt Cf1217

Yield=49%; $^{31}$P (D$_2$O): 10.18; $^1$H (D$_2$O): 1.01 (m, 2H, caproyl CH$_2$), 1.21 (m, 2H, caproyl CH$_2$), 1.32 (m, 2H, caproyl CH$_2$), 1.78 (s, 3H, 5-CH$_3$), 2.05 (m, 2H, caproyl CH$_2$), 2.58 (m, 2H, caproyl CH$_2$)$_1$ 3.78 (m, 2H, H5'), 4.99 (s, 1H, H4'), 6.32 (m, 1H, H3'), 6.82 (m, 1H, H2'), 7.51 (s, 1H, H6); 13C (D$_2$O): 11.84 (5-CH$_3$), 25.66 (caproyl CH$_2$), 26.46 (caproyl CH$_2$), 31.10 (d, J=6.82 Hz, caproyl CH$_2$), 37.06 (caproyl CH$_2$), 41.47 (caproyl CH$_2$), 65.37 (d, J=4.83 Hz, C5'), 86.45 (d, J=9.74 Hz, C4'), 90.29 (C1'), 111.43 (C5), 125.27 (C2'), 134.80 (C3'), 138.89 (C6), 152.48 (C2), 166.94 (C4), 183.15 (COO).

2',3'-Dideoxycytidine-5'-(phenyl-N-methoxyalaninyl) phosphoramidate Cf 1221

Yield=16.6%; $^{31}$P (CDCl$_3$): 3.94, 4.00; $^1$H (CDCl$_3$): 1.33, 1.35 (2×d, 3H, CH3 ala); 1.92, 1.96, 2.41 (1H, 2H, 1H, 3×m, H$_2$, H3'); 3.66 (s, 3H, OMe); 3.86–4.35 (m, 5H, H4', H5', CH ala, NH ala); 5.63 (2×d, J=7.4 Hz, H6), 6.02 (m, 1H, H-1'), 7.12–7.32 (m, 5H, Ar), 7.73 (1H, 2×d, J=7.4 Hz, H5); $^{13}$C (CDCl$_3$): 20.98 (CH$_3$ ala); 24.97, 25.11, 32.85 (C2', C3'); 50.12, 50.30 (CH$_3$ ala); 52.55 (OMe); 67.19, 67.26, 67.50 (C5'); 79.16, 79.27, 79.34 (C4'); 87.29, 87.46 (C1'); 93.48 (C5); 119.99, 120.04, 120.10, 125.05, 125.10, 129.73, 129.77 (CAr); 141.17 (C6); 150.48, 150.57 (C ipso Ar); 155.68 (C2); 165.44 (C4); 173.84, 173.94 (COala); Mass (ES$^+$) C$_{19}$H$_{25}$N$_4$O$_7$P: 475 (MNa$^+$, 100); HPLC: RT=20.53, 21.22 min.

2',3'-Dideoxy-2',3'-didehydrothymidine 5'-(phenylmethoxysarcosinylphosphate) Cf 1098

Yield=65%; $^{31}$P (CDCl$_3$): 6.80, 7.36 ppm; $^1$H (CDCl$_3$): 1.72 (s, 3H, 5CH$_3$); 2.64, 2.67 (s, 3H, NCH$_3$); 3.62 (s, 3H, OCH$_3$); 3.40–4.10 (m, 2H, CH$_2$); 4.20–4.50 (m, 2H, H5'); 4.97 (bs, 1H, H4'), 5.80–5.90 (m, 1H, H2'); 6.30–6.40 (m, 1H, H3'); 6.97 (bs, 1H, H1'); 7.00–7.30 (m, 6H, Ar+H6); 9.59 (bs, 1H, NH); $^{13}$C (CDCl$_3$): 12.35 (SCH$_3$); 34.55–34.60–34.65 (NCH$_3$); 50.67–50.78–50.87 (CH$_2$); 52.10–52.13 (OCH$_3$); 62.27–66.77–66.82 (C5'); 84.71–84.84 (C4'); 89.52–89.82 (C1'); 111.16–111.33 (C5); 120–150 (m, Ar); 127.17–127.40 (C2'); 133.25–133.62 (C3'); 135.73–136.11 (C6); 150.85–150.90. (C2); 163.84–163.87 (C4); 170.57–170.60–170.84 (COOCH$_3$); Mass: C$_{20}$H$_{24}$O$_8$N$_3$P: 488 ((M+Na)+, 100); 466 ((M+H)$^+$, 5) HPLC: RT=25.17 and 25.59 min.

2',3'-Dideoxy-2',3'-didehydrothymidine 5'-(phenylethoxysarcosinylphosphate) Cf 1133

Yield=65%; $^{31}$P (CDCl$_3$): 0.87, 7.41 ppm; $^1$H (CDCl$_3$): 1.18–1.24 (m, 2H, CH$_3$CH$_2$); 1.80 (s, 3H, 5CH$_3$); 2.68, 2.71 (s, 3H, NCH$_3$); 3.46–3.65 (m, 2H, NCH$_2$); 3.91–4.45 (m, 2H, H5'); 4.11, 4.13 (s, 3H, CH$_2$CH$_3$); 5.00 (bs, 1H, H4'; 5.82–5.88 (m, 1H, H2'); 6.33–6.37 (m, 1H, H3'); 7.00 (bs, 1H, H1'); 7.10–7.50 (m, 6H, Ar+H6); 8.75 (bs, 1H, NH) $^{13}$C (CDCl$_3$): 12.86–12.89 (5CH$_3$); 14.69 (CH$_2$CH$_3$); 35.06–35.11 (NCH$_3$); 51.35–51.43–51.51 (NCH$_2$); 61.77 (CH$_2$CH$_3$); 66.77–67.27–67.33 (C5'); 85.26–85.36 (C4'); 90.01–90.31 (C1'); 111.69–111.86 (C5); 120–151 (m, Ar); 127.–73–127.96 (C2'); 133.73–134.10 (C3'); 136.27–136.64 (C6); 151.61 (C2); 164.70 (C4); 170.62–170.66–170.85 (COOCH$_3$); Mass: C$_{21}$H$_{26}$O$_8$N$_3$P: 502 ((M+Na)+, 100); 480 ((M+H)$^+$, 5); HPLC: RT=25.84 and 26.65 min.

2',3'-Dideoxy-2',3'-didehydrothymidine 5'-(methioninyl phosphate) Cf 1156

Yield=52%; $^{31}$P (CDCl$_3$): 7.77 ppm; 1H (CDCl$_3$): 1.75–1.85 (m, 2H, CH$_2$S); 1.90 (s, 3H, SCH$_3$); 2.01, 2.10 (s, 3H, 5CH$_3$); 2.30–2.50 (m, 2H, CH$_2$CH$_2$S); 3.45–3.60 (m, 1H CHNH); 3.94 (s, 2H, H5'); 5.05 (bs, 1H, H4'); 5.90–6.00 (m, 1H, H2'); 6.40–6.50 (m, 1H, H3'); 6.93 (bs, 1H, H1'); 7.68 (s, 1H, H6); $^{13}$C (CDCl$_3$): 11.91 (5CH$_3$); 14.46 (SCH$_3$); 29.58 (CH$_3$SCH$_2$CH$_2$); 34.69 (SCH$_2$CH$_2$); 56.42 (CHNH); 65.07–65.13 (C5'); 86.39–86.52 (C4'); 90.14 (C1'); 111.70 (C5); 125.48 (C2'); 134.77 (C3'); 138.91 (C6); 152.61 (C2); 167.18 (C4); 180.84 (COOH); Mass: C15H$_{22}$O$_8$N$_3$PS: 434 ((M−1), 100); 435 ((M), 15); HPLC: RT=31.38 min.

2',3'-Dideoxy-2',3'-didehydrothymidine 5'-(glycinyl phosphate) Cf 1163

Yield=75%; $^{31}$P (CDCl$_3$): 11.72 ppm; $^1$H (CDCl$_3$): 1.83 (s, 3H, 5CH$_3$); 3.29 (d, CH$_2$, J=7.9Hz); 3.85–3.92 (m, 2H, H5'); 5.0C (s, 1H, H4'); 5.85–5.88 (m, 1H, H2'); 6.38–6.41 (m, 1H, H3'), 6.88–6.90 (bs, 1H H1'); 7.54 (s, 1H, H6); $^{13}$C (CDCl$_3$): 19.09 (5CH$_3$); 52.24 (CH$_2$); 72.74–72.81 (C5'); 93.61–93.73 (C4'); 97.57 (C1'); 119.08 (C5); 132.80 (C2'); 141.89 (C3'); 145.74 (C6); 159.87 (C2); 174.34 (C4); 186.03–186.15 (COOH); Mass: C$_{12}$H$_{16}$O$_8$N$_3$P: 360 ((M-1), 100); 361 ((M), 15); HPLC: RT=32.57 min.

2',3'-Dideoxy-2',3'-didehydrothymidine 5'-(phenylmethoxyisoleucinylphosphate) Cf 1186

Yield=82%; $^{31}$P (CDCl$_3$): 4.59, 5.16 ppm; $^1$H (CDCl$_3$): 0.91–0.99 (m, 6H, CH$_3$ +CH$_3$); 1.09–1.26 (C<u>H</u>CH$_3$); 1.28–1.56 (m, 2H, CH$_2$); 1.92, 1.97 (s, 3H, 5CH$_3$); 3.60–3.77 (m, 1H, C<u>H</u>NH); 3.77 (s, 3H, OCH$_3$); 3.88–3.99 (m, 1H, N<u>H</u>CH); 4.30–4.52 (m, 2H, H5'); 5.11–5.13 (m, 1H, H4'); 5.95–6.00 (m, 1H, H2'); 6.35–6.45 (m, 1H, H3'); 7.10–7.13 (m, 1H, H1'); 7.16–7.45 (m, 6H, Ar+H6); 8.68 (bs, H, NH); $^{13}$C (CDCl$_3$); 11. 90–11.92 (CH$_2$<u>C</u>H$_3$); 12.76–12.81 (5CH$_3$); 15. 64 (C<u>H</u>CH$_3$); 25.06–25.14 (<u>C</u>H$_2$ CHCH$_3$); 39.39–39.47–39.52–39.60 (CH$_2$); 52.61 (OCH$_3$); 59.38–59.54 (NHCH); 66.94–67. 58–67.65 (C5'); 84.91–85.04–85.16 (C4'); 89.94–90.21 (C1'); 111.75–111.87 (C5'); 120–151 (m Ar); 127.82–127.87 (C2'); 133.49–133.69 (C3'); 135.99–136.28 (C6); 151.37 (C2); 164.40 (C4); 173.53–173.59–173.64 (<u>C</u>OOCH$_3$); Mass: C23H$_{30}$O$_8$N$_3$P: 529.91 ((M+Na)$^+$, 100); HPLC: RT=30.52 and 31.14 min.

2',3'-Dideoxy-2',3'-didehydrothymidine 5'-(phenylalaninyl phosphate) Cf 1187

Yield=68%; $^{31}$P (CDCl$_3$): 7.58 ppm; $^1$H (CDCl$_3$): 1.70 (s, 3H, 5CH$_3$); 2.64–2.80 (m, 2H, C<u>H</u>$_2$Ph); 3.57–3.64 (m, 1H, C<u>H</u>NH); 3.68–3.70 (m, 2H, H5'); 4.85 (s, 1H, H4'); 5.73–5.75 (m, 1H, H2'); 6.26–6.29 (m, 1H, H3'); 6.74–6.75 (m, 1H, H1'); 7.02–7.28 (m, 5H, CH$_2$<u>Ph</u>); 7.44 (s, 1H, H6); $^{13}$C (CDCl$_3$); 11.88 (5CH$_3$); 40.92–40.97 (CH$_2$ ala); 58.27 (CH ala); 65.22–65.28 (C5'); 86.36–86.49 (C4'); 90.22 (C1'); 111.63 (C5); 125.38 (C2'); 126–129 (m, Ar); 134.74 (C3'); 138.31–138.48 (C6); 152.40 (C2); 166.81 (C4); 180.87–180.96 (COOH); Mass: C$_{19}$H$_{22}$O$_8$N$_3$P: 450 ((M-1), 100); 451 ((M$^-$, 20) HPLC: RT =32.11 min;

2',3'-Dideoxy-2',3'-didehydrothymidine 5'-(valinyl phosphate) Cf 1190

Yield=67%; $^{31}$P (CDCl$_3$): 8.35 ppm; $^1$H (CDCl$_3$): 0.72 (t, 6H, (C<u>H</u>$_3$)$_2$CH, J=7.3 Hz); 1.62–1.73 (m, 1H, (CH$_3$)$_2$C<u>H</u>); 1.77 (s, 3H, 5CH$_3$); 3.12 (dd, 1H, NHC<u>H</u>, J=5.6 Hz and 9.4 Hz); 3.80 (dd, 2H, H5', J=3.5 Hz and 4.4 Hz); 4.92 (s, 1H, H4'); 5.76–5.78 (m, 1H, H2'); 6.31–6.35 (m, 1H, H3'); 6.79–6.81 (m, 1H, H1'); 7.53 (s, 1H, H6); $^{13}$C (CDCl$_3$): 11.84 (5CH$_3$); 17.95–18.84 ((<u>C</u>H$_3$)$_2$CH); 32.30–32.38 ((CH$_3$)$_2$<u>C</u>H); 62.43 (CHNH); 65.18–65.24 (C5'); 86.43–86.58 (C4'); 90.25 (C1'); 111.65 (C5); 125.20 (C2'); 134.90 (C3'); 138.73 (C6); 152.52 (C2); 167.05 (C4); 181.27–181.31 (COOH); Mass: C$_{15}$H$_{22}$O$_8$N$_3$P: 402 ((M-1)$^-$, 100); 403 ((M)$^-$, 30); HPLC: RT=31.90 min.

2',3'-Dideoxy-2',3'-didehydrothymidine 5'-(leucinyl phosphate) Cf 1192

Yield=83%; $^{31}$P (CDCl$_3$): 7.98 ppm; $^1$H (CDCl$_3$): 0.71 (d, 6H, (C<u>H</u>$_3$)$_2$CH, J=6.5 Hz); 1.22–1.34 (m, 2H, CH$_2$); 1.34–1.71 (m, 1H, (CH$_3$)$_2$C<u>H</u>); 1.80 (s, 3H, 5CH$_3$); 3.30–3.38 (m, 1H, C<u>H</u>NH); 3.82–3.85 (m, 2H, H5'); 4.95 (s, 1H, H4'); 5.80–5.82 (m, 1H, H2'); 6.35–6.37 (m, 1H, H3'); 6.81–6.82 (m, 1H, H1'); 7.58 (s, 1H, H6); $^{13}$C (CDCl$_3$): 12.53 (5CH$_3$); 22.88–22.99 ((<u>C</u>H$_3$)$_2$CH); 25.28 (CH$_2$); 45.27–45.34 ((CH$_3$)$_2$<u>C</u>H); 56.38 (CHNH); 65.74–65.81 (C5'); 87.12–87.25 (C4'); 90.89 (C1'); 112.30 (C5); 125.99 (C2');,135.49 (C3'); 139.44 (C6); 153.12 (C2); 167.70 (C4); 183.36–183.42 (COOH); Mass: C$_{16}$H$_{24}$O$_8$N$_3$P: 416 ((M-1)$^-$, 100); 417 ((M$^-$, 20) HPLC: RT=35.02 min.

2',3'-Dideoxy-2',3'-didehydrothymidine 5'-(phenylmethoxyalaninyl phosphate) [Fast Diastereoisomer] Cf 1193

$^{31}$P (CDCl$_3$): 4.51 ppm; $^1$H (CDCl$_3$): 1.25–1.40 (m, 3H, CHC<u>H</u>$_3$); 1.86–1.90 (m, 3H, 5CH$_3$); 3.74–3.90 (m, 4H, OCH$_3$+CH ala); 4.37–4.47 (m, 2H, H5'); 5.08 (bs, 1H, H4'); 5.91–5.93 (m, 1H, H2'); 6.38–6.41 (m, 1H, H3'); 7;07–7.09 (m, 1H, H1'); 7.20–7–39 (m, 6H, Ar+H6); 9.04 (bs, 1H, NH); $^{13}$C (CDCl$_3$): 10.85 (5CH$_3$); 19.38–19.45 (CH<u>C</u>H$_3$); 48.71 (<u>C</u>HCH$_3$); 51.14 (OCH$_3$); 64.91–64.97 (C5'); 83.11–83.22 (C4'); 88.03 (C1'); 109.77 (C5); 118–149 (m, Ar); 125.84 (C2'); 131.88 (C3'); 134.44 (C6); 149.34 (C2); 162.35 (C4); 172.53–172.62 (CO ala).

2',3'-Dideoxy-2',3'-didehydrothymidine 5'-(phenylprolinyl phosphate) Cf 1194

Yield=41%; $^{31}$P (CDCl$_3$): 5.27 ppm; $^1$H (CDCl$_3$): 1.55 (s, 3H, 5CH$_3$); 1.56–2.15 (m, 4H, CHC<u>H</u>$_2$C<u>H</u>$_2$); 3.10–3.30 (m, 2H, NCH$_2$); 3.90–4.00 (m, 1H, NCH); 4.20–4.50 (m, 2H, H5'); 5.11 (s, 1H, H4'); 5.89–5.91 (m, 1H, H2'); 6.41–6.44 (m, 1H, H3'); 6.76–6.78 (m, 1H, H1'); 6.99–7.40 (m, 6H, Ar+H6); $^{13}$C (CDCl$_3$): 11.84 (5CH$_3$); 25.44–25.56 ( <u>C</u>H$_2$CH$_2$N); 31.94–32.06 (<u>C</u>H$_2$CHN); 47.40–47.46 (NCH$_2$); 63.31 (CHN); 67.14–67.21 (C5'); 85.56–85.68 (C4'); 90.69 (C1'); 111.00 (C5), 120–150 (m, Ar), 125.07 (C2'), 134.13 (C3'), 138.26 (C6), 152.67 (C2), 166.64 (C4), 181.32 (COOH); Mass: C$_{21}$H$_{24}$O$_8$N$_3$P: 476 ((M-1)$^-$, 100); 477 ((M)$^-$, 25); HPLC: RT=34.16 min.

1001 2',3'-Dideoxy-2',3' didehydroadenosine-5'-(phenyl methoxyalaninyl phosphoramidate:

Yield=67%; $^1$H (dmso-d6): 8.14 (1H, s, H8), 8.06 (1H, d, H2), 7.07–7.40 (7H, m, Phe-H & NH$_2$), 6.93 (1H, s, H1'), 6.47 (1H, 2d, H3'), 6.21 (1H, d, H3'), 5.96 (1H, n, NH), 5.11 (1H, m, H4'), 4.10 (2H, m, H5'), 3.5–4.83 (1H, 2m, CH ala), 3.52 (3H, d, MeO), 1.08 (3H, 2d, CH$_3$ ala). $^{31}$P (dmso-d6): 4.92, 4.78. $^{13}$C (dmso-d6): 172.909–172.815 (CO ala), 154.663 (C-2), 152.238 (C-6), 149.524–149.442 (Ar-ipso), 148.782 (C-4), 138.006–137.907 (C-8), 132.286–132.205 (C-2'), 128.621 (Ar-meta), 125.384–125.210 (Ar para), 123.928 (C-3'), 119.067–119.00 (Ar ortho), 118.508 (C-5), 87.311–87.060 (C-1'), 84.485–84.368 (C-4'), 66.093–65.324 (C-5'), 51.477–51.429 (OMe), 49.109–48.989 (C—H ala), 19.903–19.585 (CH$_3$ ala). Mass. Calculated MH$^+$:475.149. Found: 475.151.

1093 2',3'-Dideoxyadenosine 5'-(phenylmethoxyalaninyl) phosphoramidate

Yield=42%; $^1$H (CDCl$_3$): 8.32 (1H, s, H-8), 8 .12 & 8.11 (1H, 2s, H-2) 7.22 (5H, m, Ar), 6.40 (2H, 2bs, NH$_2$), 6.30 (1H, t, H-1', J=5.4 Hz), 4.42 (4H, m, N—H, 2H5' & H4'), 4.00 (1H, 2d, Ala C—H), 3.65 (3H, 2s, OMe), 2.52 (2H, m, H3'), 2.13 (2H, m, H2'), 1.31 (3H, 2d, CH$_3$ ala, J=7.3 Hz). $^{31}$P (CDCl$_3$): 4.26, 4.19. $^{13}$C nmr (CDCl$_3$): 174.534, 174.468, 174.441, 174.372 (O—C=O), 156.148 (C-2), 153.331 (C-6), 151.092 & 151.006 (2 Ar ipso), 149.674 & 149.599 (C-4), 139.211 & 139.103 (C-8), 130.040 (Ar meta), 125.325 (Ar para), 120.570 (C-5), 120.508 & 120.327 (Ar ortho), 85.994 & 85.746 (C-1'), 80.105, 79.985 & 79.874 (C-4'), 68.136, 68.067, 67.704 & 67.636 (C-5'), 52.868 (OMe), 50.628 & 50.531 (Ala C—H), 32.712 (C-2'), 26.339 & 26.106 (C-3'), 21.337, 21.264 & 21.190 (CH$_3$ ala). Mass: Calculated MH$^+$: 477.165. Found: 477.164.

1094 2',3'-Dideoxy-2',3' didehydroadenosine 5'-(phenyl benzylalaninyl)phosphoramidate:

Yield=65%; $^1$H (CDCl$_3$): 8.32 (1H, bs, H-8), 7.99 (1H, bs, H-2), 7.21 (11H, m, Ar—H & H1'), 6.34 (1H, m, H3'), 6.07 (1H, m, H2'), 5.81 (2H, 2bs, NH$_2$), 5.08 (3H, 2bs, Bz-CH$_2$ & H4'), 4.05 (4H, m, NH, CH, H5'), 1.24 (3H, 2d, methyl ala, J=6.9 Hz). $^{31}$P (CDCl$_3$): 4.21, 3.98; $^{13}$C (CDCl$_3$):

173.700 & 173.601 (O—C=O), 156.005 (C-2), 153.728 (C-6), 150.952 & 150.870 (Ar), 150.322 & 150.280 (C-4), 139.484 & 139.368 (C-8), 135.672 (Ar), 133.733 & 133.654 (C-2'), 130.066 (Ar), 129.041, 128.895, 128.635 & 128.601 (Ar), 126.751 & 126.598 (C-3'), 125.375 (Ar), 120.529, 120.463, 120.399, 120.119 & 120.051 (C-5 & Ar), 88.702 & 88.476 (C-1'), 85.907, 85.476, 85.791 & 85.736 (C-4'), 67.632, 67.475 & 67.403 (C-5' and Bz-CH$_2$), 66.805 & 66.745 (C-5'), 50.677 & 50.542 (Ala C—H), 21.399, 21–335, 21.083 & 21.019 (methyl Ala). Mass: Calculated MH$^+$: 551.181. Found: 551.179.

1168 2',3'-Dideoxy-2',3'-didehydroadenosine 5'-alaninyl phoshoramidate

Yield=69%; $^1$H nmr (D$_2$O): 8.09 (1H, s, H8), 7.88 (1H, s, H2), 6.81 (1H, s, H1'), 6.33 (1H, d, H3'), 6.02 (1H, d, H3'), 5.01 (1H, m, H4'), 4.73 (2H, m, H5'), 3.5–4.83 (1H, 2m, CH ala), 0.89 (3H, 2d, CH$_3$ ala). 31P (D$_2$O) 8.34. $^{13}$C (D$_2$O): 183.055 (CO ala), 155.549 (C-2), 152.745 (C-6), 148.643 (C-3), 140.928 (C-8), 134.730 (C-2'), 124.709 (C-3'), 118.527 (C-5), 88.299 (C-1'), 87.199 & 87.073 (C-4'), 65.215–65.149 (C-5'), 52.564 (Alal C—H), 21.435–21.381 (Ala CH$_3$).

1196—2',3'-Dideoxy-2',3'-didehydrothymidine-5'-(phenyl dimethoxy glutaminyl phosphoramidate Yield 33%; $^{31}$P (CDCl$_2$) 4.14, 4.76; $^1$H (CDCl$_3$) 1.81, 1.85 (5CH$_3$); 1.91–2.18 (m, 2H, CH$_2$ Gln); 2.24–2.36 (m, 2H, CH$_2$ Gln); 3.64 (s, 3H, NMe); 3.69 (s, 3H, OMe); 3.92–4.21 (m, 2H, H5'); 4.23–4.42 (m, 2H, CH Gln, NH Gln); 5.00 (m, 1H, H4'); 5.91 (m, 1H, H2'); 6.31 (m, 1H, H3'); 7.01 (m, 1H, H1'), 7.03–7.34 (m, 6H, Ph, H6); 9.49 (s, 1H, NH); $^{13}$C (CDCl$_3$) 12.32–12.36 (5CH$_3$); 29.01–29.42 (CH$_2$Gln); 29.46 (NMe); 51.81 (CH$_2$Gln); 52.65 (OMe); 53.65–53.92 (CH$_2$Gln); 66.63–67.33 (C5'); 84.48–84.71 (C4'); 89.57–89.83 (C1'); 111.29–111.44 (C5); 119.98–120.22 (Ph); 125.21–125.26 (Ph); 127.39–127.50 (C2'); 129.74–129.78 (Ph); 133.00–133.25 (C3'); 135.60–135.90 (C6); 150.98 (C2); 164.00–164.09 (C4); 172.96–173.23 (CO, CON); Mass (ES): C$_{23}$H$_{29}$N$_4$O$_9$P: 536 (M$^+$, 100); 537 (MH$^+$, 32).

1214—2',3'-Dideoxy-2',3'-didehydrothymidine-5'-(phenyl dimethoxy asparaginyl)phosphoramidate Yield 75%; $^{31}$P (CDCl$_3$) 1.15, 2.20; $^1$H (CDCl$_3$) 1.81, 1.86 (s, 3H, 5CH$_3$); 2.49–2.92 (m, 2H, CH$_2$ Asn); 3.64 (s, 3H, NMe); 3.72 (s, 3H, OMe); 4.04–4.26 (m, 2H, H5'); 4.28–4.43 (m, 2H, CH Asn, NH Asn); 5.05 (m, 1H, H4'); 5.89 (m, 1H, H2'); 6.31 (m, 1H, H3'); 7.01 (m, 1H, H1'); 7.14–7.33 (m, 6H, Ph, H6); 8.46 (s, 1H, NH); $^{13}$C (CDCl$_3$) 12.28 (5CH$_3$); 51.01 (CH Asn); 52.09 (OMe); 52.94 (CH$_2$ Asn); 84.75 (C4'); 89.60 (C1'); 111.30 (C5); 125–130 (Ph); 127.32–127.48 (C2'); 133.10–133.41 (C3'); 135.94 (C6); 50 Mass (ES): C$_{22}$H$_{27}$N$_4$O$_9$P: 522 (M$^+$, 100); 523 (MH$^+$, 31).

1215—2',3'-Dideoxy-2',3'-didehydrothymidine-5'-(phenyl methoxytryptophanyl)phosphoramidate Yield 100%; $^3$P (CDCl$_3$) 4.15, 4.57; $^1$H (CDCl$_3$) 1.74 (s, 3H, 5CH$_3$); 3.16 (m, 2H, CH$_2$Trp); 3.60 (s, 3H, OMe); 3.75–4.05 (m, 2H, H5'); 4.10–4.33 (m, 2H, CH Trp NH Trp); 4.84 (m, 1H, H4'); 5.79 (m, 1H, H2'); 6.15 (m, 1H, H3'); 6.86 (m, 1H, H1'); 6.91 (m, 1H, H6); 7.00–7.49 (m, 10H, Ar); 8.45 (s, 1H, NH Trp); 9.14 (s, 1H, NH); $^{13}$C (CDCl$_3$) 14.75 (5CH$_3$); 32.46 (CH$_2$ Trp); 54.91 (CH Trp); 57.53–57.61 (OMe); 69 (C5'); 87.06 (C4'); 92.03–92.25 (C1'); 111.63 (C5); 127.60 (C2'); 135.45–135.83 (C3'); 138.11–138.62 (C6); 152.78–153.41 (C2); 166.28–166.40 (C4); 175.85 (CO); Mass (ES): C$_{28}$H$_{28}$N$_4$O$_9$P: 579 (M$^+$, 100); 580 (M$^+$, 43).

462 3'-Deoxy-3'-β-azidothymidine 5'-(phenyl methoxylalaninyl) phosphoramidate $^1$H (CDCl$_3$): 1.39 (d, 3H, J=7.2 Hz, CH$_3$ ala), 1.94 (s, 3H 5-Me), Me), 2.15 (d, 1H, J=15.5 Hz, H2'), 2.68–2.79 (m, 1H, H2'), 3.72 (s, 3H, OMe), 3.90–4.50 (m, 6H, H3'+H4'+H5'+NH+CHala), 6.18 (dd, 1H, J=7.5 and 3.1 Hz, H1'), 7.1–7.4 (m, 6H, Ph+H6), 8.82 (bs, 1H, NH). $^{13}$C (CDCl$_3$): 12.67 (5-Me), 20.96, 21.29 (ala-Me), 38.50 (C2'), 50.16, 50.28 (CHala), 52.57 (OMeala), 60.74 (C3'), 64.43 (C5'), 80.17 (C4'), 83.93 (C1'), 111.21 (C5), 120.11 (Ar2), 125.18 (Ar4), 129.73 (Ar3), 135.18 (C6), 159.96 (Ar1), 150.30 (C4), 163.49 (C2), 173.84 (COala). $^{31}$P (CDCl$_3$): 1.55; IR (CDCl$_3$): 3216, 2113, 1685 cm-1. Mass 509.1543 (MH$_+$, 40%, calculated 509.1549), 340(12), 250(17), 200(18). HPLC: RT=28.48 min.

536 3'-Deoxy-3'β-azidothymidine 5'-(m-trifluoromethylphenyl methoxylalaninyl)phosphoramidate $^1$H (CDCl$_3$): 1.39, 1.40 (d, 3H, J=7.2 Hz, Me-ala), 1.92, 1.93 (s, 3H, 5-CH$_3$), 2.15 (d, 1H, J=15.1 Hz, H2'), 2.71–2.80 (m, 1H, H2'), 3.70, 3.71 (s, 3H, OMe), 3.90–4.50 (m, 6H, H3'+H4'+H5'+NH+CHala), 6.19 (dd, 1H, J=7.7 and 3.3 Hz, H1'), 7.41–7.46 (m, 5H, Ph+H6), 9.52 (bs, 1H, NH). $^{13}$C (CDCl$_3$): 12.58 (5-Me), 20.75, 20.83 (CH$_3$ ala), 38.33, 38.44 (C2'), 50.15, 50.29 (CHala), 52.55 (OMeala), 60.77 (C3'), 64.72 (C5'), 80.05, 80.35 (d, J=6.8 Hz, C4'), 83.94 (C1'), 111.25 (C5), 117.43 (Ar2), 121.81, 121.86 (Ar4), 123.37 (q, J=273 Hz, CF$_3$), 123.74 (Ar6), 130.35 (Ar5), 132.11 (q, J=33 Hz, Ar3), 135.11 (C6), 150.49 (C4), 150.62 (Ar1), 163.78 (C2), 173.68, 173.87 (d, J=7.8 Hz, COala). $^{31}$P: 2.69; Mass 577 (MH$^+$, 40%) 340 (13), 268 (14), 250 (12). HPLC: RT=30.66 min.

550 3'-Deoxy-3'-β-azidothymidine 5'-(3,5-dichlorophenyl methoxylalaninyl)phosphoramidate $^1$H (CDCl$_3$): 1.42 (d, 3H, J=6.8 Hz, Me-ala), 1.94, 1.95 (d, 3H, J=1.2 Hz, 5-CH$_3$), 2.17, 2.18 (d, 1H, J=15.1 Hz, 2'), 2.76–2.85 (m, 1H, H2'), 3.74, 3.75 (s, 3H, OMe), 3.90–450 (m, 6H, H3'+H4'+H5'+NH+CHala), 6.20 (dd, 1H, J=7.7 and 3.3 Hz, H1'), 7.19 (m, 2H, Ar2), 7.27 (s, 1H, Ar4), 7.41, 7.42 (s, 1H, H6), 9.04 (bs, 1H, NH). $^{13}$C: 12.65 (5-Me), 20.85, 20.91 (CH$_3$ ala), 38.38, 38.48 (C2'), 50.18, 50.29 (CHala), 52.68 (OMeala), 60.77 (C3'), 64.86, 64.93 (C5'), 79.80, 80.20 (d, J=8 Hz, C4'), 83.97 (C1'), 111.35 (C5), 117.28, 119.38 (d, J=6 Hz, Ar2), 125. 58 (Ar4), 135.10 (C6), 135.46, 135.50 (Ar3), 145.35 (Ar1), 150.36 (C4), 163.61 (C2), 173.64, 173.79 (COala). $^{31}$P: 2.83; Mass 577, 579, 581 (MH$_+$ 5:3:1:) 307, 309, 311 (12:8:2) 289 (10).

In vitro Testing

Cells were infected with HIV-1 as previously described [Balzarini et al. AIDS (1991), 5, 21–28]. Briefly, 5×10$_5$ cells per milliliter were infected with HIV-1 or HIV-2 at 100 CCID$_{50}$ (50% cell culture infective dose) per milliliter of cell suspension. Then 100 μL of the infected cell suspension was transferred to microtiter plate wells and mixed with 100 μL of the appropriate dilutions of the test compounds. After 4 days giant cell formation was recorded microscopically in the HIV-infected cell cultures [CEM], and after 5 days the number of viable cells was determined by trypan blue staining of the HIV-infected cell cultures [MT4]. The 50% effective concentration (EC$_{50}$) and 50% cytoxic concentration (CC$_{50}$) were defined as the compound concentrations required to reduce by 50% the number of giant cells or viable cells in the virus-infected and mock-infected cell cultures, respectively.

The anti-HIV-1 activities and toxicities of compounds were also assessed in two cell lines:

C8166 cells. Cells were grown in RPMI 1640 with 10% calf serum. 4×10$^4$ cells per microtiter plate well were mixed with 5-fold dilutions of compound prior to addition of 10 CCID$_{50}$ units of III-B strain of HIV-1 and incubated for 5–7 days (Betbeder et al. Antiviral Chem. Chemother. 1, 241–247, 1990). Formation of syncytia was examined from 2 days post-infection. Culture fluid was collected at 5–7 days and gp120 antigen production measured by ELISA (Mahmood and Hay, J. Immunol. Meth., 151, 9–13, 1992). The $EC_{50}$ is that concentration of drug [in $\mu$M] required to reduce gp120 production by 50%. Cell viability of infected and uninfected cells were assessed by the MTT-Formazen method (Pauwels et al. J. Virol. Meth. 20, 309–321, 1988).

JM cells JM cells, which are relatively resistant to the antiviral effects of AZT and a number of its derivatives, were infected with HIV-1 strains and the antiviral and toxic effects of compounds assessed as for C8166 cells. both GB8 or IIIB strains of HIV1 were used, with no detactable differences in the end-points noted.

Each assay was carried out in duplicate on at least two separate occasions, and data quoted are the average of each separate assay.

The compounds of the present invention have been shown to be active against both HIV1 and HIV2 in both TK$^-$ and TK$^+$ cells as illustrated in Table 2.

TABLE 2

| Compound | $EC_{50}$ $\mu$M C8166 | $EC_{50}$ JM | $EC_{50}$ $\mu$M CEM TK* | $EC_{50}$ CEM TK* |
|---|---|---|---|---|
| | | | HIV2 in CEM TK*/CEM TK* | |
| 730 | 0.0008 | 0.0008 | 0.06 | 0.06 |
| d4T (comparative) | 0.08 | 0.8 | 1.2 | >100 |

As expected, d4T (comparative) loses activity in kinase deficient cells (especially GEM TK$^+$), whilst compound 730 of the invention retains good activity in both TK$^-$ and TK$^+$ against both HIV1 and HIV2. Compound 730 of the invention is >1000 times more potent than d4T in TK$^+$ cells. Surprisingly, the compound is 100-fold more potent than d4T in CEM TK$^-$ assays.

The potent activity of the compounds of the invention is further supported by the data in Table 3, which illustrates activity, toxicity and selectivity index of a series of compounds of the present invention.

The enhance anti-viral potency and reduced cytotoxicity of the phosphate derivatives lead to very large improvements in selectivity index [defined as $CC_{50}/EC_{50}$] evidencing marked improvements in in vivo efficacy compared to d4T (comparative).

Evidence that the compounds of the present invention are acting via a pathway different to that of d4T or AZT is provided by the data of Table 4.

As can be seen, whilst the potency of d4T (comparative) is much reduced in nucleoside resistant strains, the potency of the compounds of the present invention is largely maintained. Thus, it is clear that the compounds of the present invention are not acting primarily via the conventional nucleoside 5'triphosphate derivative.

CEM and MT4 cells (at 400,000 cells/ml) and PBL cells (at 2,000,000 cells/ml) were exposed to different concentrations of [$^3$H] 324 and incubated at 37° C. for 24 hours. Then cells were washed twice with cold PBS and to the cell pellet was added 400 $\mu$l cold methanol 66%. After standing on ice for 10 min, the cell extract was centrifuged and the supernatent analayzed on HPLC. As shown in Table 5, intracellular D4T-MP (monophosphate) levels increased proportionally in function of the initial concentration of 324 in all three cell lines tested. However, the increase of D4T-TP (triphosphate) levels slowed down at initial 324 concentrations that were higher than 25 $\mu$M (for CEM and MT4 cells) or higher than 1.0 $\mu$M (for PBL). Surprisingly, a metabolite (designated X) accumulated substantially and predominantly in all three cell types. The accumulation was proportional to the initial 324 concentration, and, again, was lower in PBL than CEM and MT4 cells.

When 1 mM 324 was incubated with high concentrations of hog liver esterase at 37° C. in Tris-HCl buffer containing 5 mM $MgCl_2$, a time-dependent formation of a metabolite was observed. This metabolites co-eluted with the predominant metabolite (X) that was found in the cell extracts after incubation of the intact cells with [$^3$H] 324. Metabolite X corresponds to a compound of formula (10), wherein Y is oxygen, X$^1$ is NH, X$^2$ is oxygen, B is thymine, R$^1$ is Me, R$^2$ is hydrogen.

Data on an expanded range of compounds is presented in Table 6 (d4T analogues) and Table 7 (dideoxy and 3'-$\beta$-substituted nucleoside analogues) in which:

Cpd and Init: refer to the compound reference numbers;

Y: refers to the group:

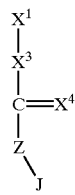

Z: refers to the 3'-substituent on a deoxyribose sugar wherein the substituent is in an "α" orientation (R$^9$) unless designated "up" which refers to a "β" orientation (R$^{10}$);

B: refers to the heterocyclic nucleic acid base, present at C1' in β-orientation; conventional one-letter base codes are used; pyrimidine substituents are at C5.

The data columns are, in order:

HIV1 MT4: $EC_{50}$ in $\mu$M for inhibition of HIV-1 in MT4 cells.

HIV2 MT4: $EC_{50}$ in $\mu$M for inhibition of HIV-2 in MT4 cells.

CC50 MT4: $CC_{50}$ in $\mu$M for toxicity to MT-4 cells.

HIV1 CEM: $EC_{50}$ in $\mu$M for inhibition of HIV-1 in CEM cells.

HIV2 CEM: $EC_{50}$ in $\mu$M for inhibition of HIV-2 in CEM cells.

HIV2 CEM-TK$^-$: $EC_{50}$ in $\mu$M for inhibition of HIV-2 in CEM/TK$^-$ cells.

CC50 CEM: $CC_{50}$ in $\mu$M for toxicity to CEM cells.

EC50 MSV: $EC_{50}$ in $\mu$M for inhibition of MSV

MCC MSV: Minimum cytotoxic concentration in MSV assay

Where data of table 6 differs from that presented in Tables 2 to 5, the data of the former relates to the mean result obtained from two or more repeat experiments, whereas the latter relates to individual experimental results.

TABLE 3

| Entry | Ar | R¹ | J | Activity EC$_{50}$ | Toxicity CC$_{50}$ | Selectivity CC$_{50}$/ EC$_{50}$ × 10$^3$ |
|---|---|---|---|---|---|---|
| 323 | 4-EtPh | Me | Me | 0.0032 | 50 | 15.6 |
| 324 | Ph | Me | Me | 0.0032 | 150 | 46.9 |
| 327 | 4-FPh | Me | Me | 0.0032 | 200 | 62.5 |
| 526 | 3-CF$_2$Ph | Me | Me | 0.0008 | 200 | 250 |
| 546 | 3,5-Cl$_2$Ph | Me | Me | 0.001 | 100 | 100 |
| 730 | Ph | Me | Bzl | 0.0008 | 400 | 500 |
| 776 | 2,4-Br$_2$Ph | Me | Me | 0.0008 | 100 | 125 |
| 779 | F$_5$Ph | Me | Me | 0.064 | 80 | 1.25 |
| 862 | Ph | Me | Hex | 0.0012 | 500 | 417 |
| 863 | Ph | Me | Me | 0.016 | 500 | 31.2 |
| 864 | Ph | CH$_2$iPr | Me | 0.016 | >1000 | >62.5 |
| 865 | Ph | iPr | Me | 0.8 | >1000 | >1.25 |
| 866 | Ph | H | Me | 0.8 | >1000 | >1.25 |
| 867 | Ph | [CH$_2$]$_2$SMe | Me | 0.0016 | >1000 | >62.5 |
| 868 | 2,4Br$_2$Ph | Me | Bzl | 0.0032 | 500 | 156 |
| 877 | Ph | Bzl | Bzl | 0.0003 | 80 | 267 |
| 878 | Ph | Bzl | tBu | 0.16 | 150 | 0.9 |
| 892 | Ph | Me | Cyclohex | 0.0016 | 500 | 312 |
| 893 | Ph | Me | tBu | 0.2 | >1000 | >5.0 |

[data are μM for HIV1 in C8166 cells]
By comparison, similar data for d4T:

| | | | | | | |
|---|---|---|---|---|---|---|
| d4T | — | — | — | 0.08 | 50 | 0.6 |

TABLE 4

| Compound | EC$_{50}$ in μM HIV RT | EC$_{50}$ 8166 HIV1 | SI 8166 HIV1 | EC$_{50}$ CEM HIV1 | EC$_{50}$ CEM TK HIV2 | EC$_{50}$ HeLa HIV1 d4T-Sensitive | EC$_{50}$ HeLa HIV1 d4T-Resistant |
|---|---|---|---|---|---|---|---|
| d4T | Inactive | 0.08 | 625 | 0.5 | >100 | 0.86 | 3.38 |
| 324 | 50 | 0.0032 | 62,500 | 0.18 | 0.08 | n/d | n/d |
| 526 | n/d | 0.0008 | >250,000 | 0.08 | 0.06 | 0.04 | 0.05 |
| 546 | n/d | 0.001 | >200,000 | 0.06 | 0.06 | 0.03 | 0.04 |
| AZT | Inactive | 0.008 | >100,000 | 0.003 | >100 | n/d | n/d |

TABLE 5

Metabolism of [³H] 324 after 24 hr incubation in human CEM, MT4 and PBL cells nmole/10$^9$ cells

| | CEM | | | | | | MT-4 | | PBL | | |
|---|---|---|---|---|---|---|---|---|---|---|---|
| | Initial concentration of [³H] 324 (μM) | | | | | | | | | | |
| Metabolite | 0.2 | 1.0 | 5.0 | 25 | 100 | 500 | 0.2 | 25 | 0.2 | 1.0 | 25 |
| 324 + D4T | 7.6 | 47.8 | 228 | 897 | 4,333 | 16,691 | 7.9 | 1,255 | 2.0 | 12.2 | 245 |
| D4T-MP | 3.9 | 10.8 | 54 | 490 | 2,259 | 11,359 | 29 | 394 | 2.4 | 14.2 | 355 |
| D4T-DP | 1.5 | 5.1 | 21.6 | 75 | 214 | 430 | 2.0 | 116 | 0.45 | 1.8 | 15.3 |
| D4T-TP | 30.3 | 37.6 | 177 | 553 | 691 | 938 | 22.6 | 535 | 6.6 | 27 | 149 |
| | 133 | 628 | 3,164 | 16,193 | 66,359 | 204,442 | 117 | 14,582 | 17.6 | 97.3 | 1,995 |

TABLE 6

| Cpd | Init | ArO | Y | Z | B | HIV1 MT | HIV2 MT | CC50 MT | HIV1 CEM | HIV2 CEM | 2.CEM.TK | CC50 CEM | EC50 MS | MCCMS |
|---|---|---|---|---|---|---|---|---|---|---|---|---|---|---|
| 268 | AS | — | HexO | = | T | | | | 0.24 | 1.2 | >100 | 36 | | |
| 321 | AS/DC | HexO | MeValNH | = | T | | | | >42 | >42 | >42 | | | |
| 322 | AS | TCEO | MeAlaNH | = | T | | | | 29 | 71 | 59 | | | |
| 323 | AS | EtPhO | MeAlaNH | = | T | 0.057 | 0.063 | >100 | 0.07 | 0.16 | 0.06 | 60 | | |
| 324 | AS/DC | PhO | MePheNH | = | T | 0.081 | 0.063 | >100 | 0.075 | 0.075 | 0.075 | 100 | | |
| 325 | AS | TCEO | MeAlaNH | = | T | 0.44 | 0.5 | >100 | 1 | 2 | 0.7 | | | |
| 326 | AS | PrO | MeAlaNH | = | T | 36 | 84 | >250 | >230 | >230 | 135 | ≧250 | | |
| 345 | AS | TCEO | MeMetNH | = | T | | | | 8 | 11 | 10 | | | |
| 400 | AS | TCEO | PntNH | = | T | | | | >40 | >40 | >40 | | | |
| 401 | AS | TCEO | PrNH | = | T | | | | >210 | >210 | >210 | | | |
| 402 | AS | TCEO | BuNH | = | T | | | | 118 | 204 | 161 | | | |
| 403 | AS | TCEO | EtNH | = | T | | | | >216 | >216 | >218 | | | |
| 404 | AS | TCEO | PrO | = | T | | | | >209 | >209 | >209 | | | |
| 406 | AS | TCEO | MeOCH2CH2N | = | T | | | | >203 | >203 | >203 | | | |
| 407 | AS | TCEO | HO | = | T | | | | 0.5 | 0.5 | 86 | | | |
| 446 | AS | — | — | = | U | | | | >95 | >95 | >95 | | | |
| 479 | ST | iPrO | iPrO 5'-PNH | = | T | | | | >258 | >258 | >258 | | | |
| 480 | ST | BuO | BuO 5'-PNH | = | T | | | | >48 | >48 | >48 | | | |
| 481 | ST | BuO | BuO 5'-PNMe | = | T | | | | >9 | >9 | >9 | | | |
| 504 | AS | TFEO | BuNH | = | U | | | | 73 | 116 | ≧226 | | | |
| 526 | AS | mCF3PhO | MeAlaNH | = | T | 0.05 | 0.11 | 10 | 0.15 | 0.15 | 0.12 | 30 | | |
| 546 | AS | 3,5-Cl2PhO | MeAlaNH | = | T | 0.037 | 0.12 | 10.5 | 0.12 | 0.15 | 0.12 | 26.9 | | |
| 547 | AS | mTFMPhO | MeAlaNH | = | U | | | | >3520 | >7 | >35 | | | |
| 551 | AS | EtO | EtO | = | U | | | | >58 | >58 | >58 | | | |
| 558 | AS | EtO | MeAlaNH | = | U | | | | >44 | >44 | >44 | | | |
| 561 | AS | FPhO | MeAlaNH | = | T | | | | 85 | 4 | ≧72 | | | |
| 562 | AS | TCEO | TCEO | = | T | | | | >36 | >36 | >36 | | | |
| 563 | AS | EtO | PrNH | = | T | | | | >268 | >268 | >268 | | | |
| 564 | AS | EtO | MeAlaNH | = | T | 28.5 | 62.5 | ≧250 | >48 | >240 | >48 | ≧250 | | |
| 730 | DC | PhO | BzAlaNH | = | T | 25.4 | 50.9 | >250 | 0.016 | 0.016 | 0.06 | 25 | | |
| 740 | DC | MeO | MeAlaNH | = | T | | | | 20 | 50 | >250 | >250 | | |
| 775 | DC | HO | HO | = | T | | | | 0.8 | 0.95 | 33 | 174 | | |
| 776 | DC | 2,4-Br2PhO | MeAlaNh | = | T | | | | 0.04 | 0.055 | 0.025 | 16 | | |
| 779 | DC | F5PhO | MeAlaNH | = | T | 1.72 | 4.07 | 82 | 2.5 | 3.7 | 8.5 | 115 | | |
| 786 | DC | HexO | H | = | T | | | | 0.8 | 0.5 | 30 | 150 | | |
| 787 | DC | MeODigolO | H | = | T | | | | 0.65 | 0.95 | 45 | 144 | | |
| 788 | DC | EtO | H | = | T | | | | 0.65 | 0.6 | 30 | 115 | | |
| 789 | DC | DecO | H | = | T | | | | 0.65 | 0.65 | 40 | 64 | | |
| 790 | DC | BuO | H | = | T | | | | 0.65 | 0.9 | 30 | 177 | | |
| 791 | DC | OctO | H | = | T | | | | 0.4 | 0.6 | 23 | 90 | | |
| 792 | DC | PntO | H | = | T | | | | 0.55 | 0.9 | 40 | 137 | | |
| 793 | DC | PrO | H | = | T | | | | 0.65 | 0.65 | 33 | 170 | | |
| 816 | DC | C16O | H | = | T | | | | 0.85 | 0.65 | 15 | 25 | | |
| 817 | DC | MeO | H | = | T | | | | 0.7 | 0.55 | 20 | 146 | | |
| 828 | DC | PhO | C12NH | = | T | | | | >10 | >10 | | 14 | | |
| 829 | DC | PhO | C8NH | = | T | | | | >10 | >10 | | ≧250 | | |
| 830 | DC | PhO | BuNH | = | T | | | | 140 | 100 | 125 | 115 | | |
| 849 | DC | PhO | BzAlaNH | = | U | | | | 23 | 15 | 10 | | | |
| 853 | DC | PhO | OH | = | T | | | | 0.65 | 0.7 | 23 | 153 | | |

TABLE 6-continued

| Cpd | Init | ArO | Y | Z | B | HIV1 MT | HIV2 MT | CC50 MT | HIV1 CEM | HIV2 CEM | 2.CEM.TK | CC50 CEM | EC50 MS | MCCMS |
|---|---|---|---|---|---|---|---|---|---|---|---|---|---|---|
| 858 | DC | PhO | PrNH | = | T | | | | >250 | >250 | >250 | >250 | | |
| 859 | DC | PhO | HxNH | = | T | | | | >50 | >50 | >50 | 145 | | |
| 860 | DC | PhO | PntNH | = | T | | | | >250 | >250 | >250 | ≧250 | | |
| 861 | DC | PhO | CNEO | = | T | | | | 1.2 | 0.95 | 17.5 | ≧250 | | |
| 862 | DC | PhO | HxAlaNH | = | T | | | | 0.06 | 0.055 | 0.033 | 48 | | |
| 863 | DC | PhO | MePheNH | = | T | 0.2 | 0.4 | 34 | 0.8 | 1.35 | 0.33 | 216 | | |
| 864 | DC | PhO | MeLeuNH | = | T | 0.2 | 0.5 | 62 | 1.1 | 2.23 | 0.4 | ≧250 | | |
| 865 | DC | PhO | MeValNH | = | T | 3.6 | 11.2 | >250 | 12.5 | 12.5 | 4 | >250 | | |
| 866 | DC | PhO | MeGlyNH | = | T | 1.3 | 6.7 | ≧250 | 6 | 6 | 7 | ≧250 | | |
| 867 | DC | PhO | MeMetNH | = | T | 0.2 | 0.4 | 22 | 0.6 | 0.8 | 0.34 | ≧250 | | |
| 868 | DC | Br2PhO | BzAlaNH | = | T | | | | 0.2 | 0.2 | 0.2 | 50 | | |
| 870 | DC | Br2PhO | BzAlaNH | = | U | | | | >50 | >50 | 12.5 | 180 | | |
| 877 | DC | PhO | BzPheNH | = | T | | | | 0.6 | 0.6 | 0.24 | 44 | | |
| 878 | DC | PhO | tBuPheNH | = | T | | | | 2 | 2 | 0.65 | 80 | | |
| 879 | DC | PhO | MeProNH | = | T | | | | >10 | >10 | >10 | 42.5 | | |
| 880 | DC | PhO | PhO | = | T | | | | 25 | 25 | 75 | ≧250 | | |
| 881 | DC | HO | NH2AlaNH | = | T | | | | | | | | | |
| 892 | GO/DC | PhO | CHxAlaNH | = | T | | | | 0.065 | 0.075 | 0.09 | 51.4 | | |
| 893 | GO/DC | PhO | tBuAlaNH | = | T | | | | 0.85 | 1.1 | 0.74 | ≧250 | | |
| 932 | ASS | PhO | Me-D-AlaNH | = | T | | | | 3 | 2 | 2.5 | ≧250 | | |
| 933 | DC | PhO | BzProNH | = | T | | | | 35 | 12.5 | >50 | 92 | | |
| 949 | DC | PhO | EtMetNH | = | T | | | | 0.8 | 0.3 | 0.15 | 166 | >100 | >100 |
| 950 | DC | PhO | Et-b-AlaNH | = | T | | | | 250 | ≧250 | >250 | >250 | 52 | >100 |
| 951 | DC | PhO | EtAlaNH | = | T | | | | 0.1 | 0.07 | 0.07 | 55 | >100 | >100 |
| 978 | DC | PhO | MeLactO | = | T | | | | 40 | 50 | >250 | ≧250 | 25 | >100 |
| 979 | DC | PhO | EtLactO | = | T | | | | 28 | 23 | 160 | ≧250 | >100 | >100 |
| 980 | DC | PhO | MeGlycO | = | T | | | | 27.5 | 50 | >250 | >250 | >100 | >100 |
| 981 | DC | PhO | EtGlycO | = | T | | | | 12.5 | 12.5 | 150 | ≧250 | >100 | >100 |
| 982 | DC | PhO | MeMandO | = | T | | | | 1.7 | 0.65 | 15 | 94 | 14 | >100 |
| 983 | DC | N-MeEphedrine | heterocycle | = | T | | | | ≧250 | 122 | >250 | >250 | >100 | >100 |
| 1078 | SV | PhO | Me2AspNH | = | T | | | | 0.55 | 0.65 | 0.33 | 209 | 31.4 | >100 |
| 1079 | SV | HO | AspNH | = | T | | | | 1.8 | 2.5 | 70 | ≧250 | 9.3 | >100 |
| 1080 | SV | HO | MeAspNH[SC] | = | T | | | | 3.5 | 5 | 110 | ≧250 | 30.3 | >100 |
| 1081 | ASS | PhO | Me2GluNH | = | T | | | | 8 | 5.33 | 1.6 | ≧250 | 88.8 | >100 |
| 1083 | ASS | HO | GluNH | = | T | | | | 8.5 | 5.5 | >250 | ≧250 | 54.6 | >100 |
| 1095 | ASS | HO | D-AlaNH | = | T | | | | 1.3 | 1.5 | 10 | >250 | 0.42 | >100 |

TABLE 6-continued

| Cpd | Init | ArO | Y | Z | B | HIV1 MT | HIV2 MT | CC50 MT | HIV1 CEM | HIV2 CEM | 2.CEM.TK | CC50 CEM | EC50 MS | MCCMS |
|---|---|---|---|---|---|---|---|---|---|---|---|---|---|---|
| 1129 | SV | HO | MeAlaNH | = | T | | | | 2 | 4.5 | 50 | >250 | 47.4 | >100 |
| 1131 | SV | OH | OH | = | T | | | | 0.4 | 0.6 | 50 | ≧250 | 6.7 | >100 |
| 1133 | LB | PhO | EtOGlyNMe | = | T | | | | 75 | 87.5 | >250 | ≧250 | >100 | >100 |
| 1135 | SV | MeO | BzAlaNH | = | T | | | | 10 | 15 | 17.5 | >250 | >100 | >100 |
| 1137 | SV | OH | BzAlaNH | = | T | | | | 0.95 | 1.6 | 8 | ≧250 | 15.7 | >100 |
| 1139 | MW | PhO | OC10OH | = | T | | | | 15 | 15 | >50 | 66.6 | >20 | >20 |
| 1156 | LB | HO | MetNH | = | T | | | | 1.27 | 0.7 | 50 | >250 | 16.2 | >100 |
| 1163 | LB | HO | GlyNH | = | T | | | | 2 | 5 | 130 | >250 | | |
| 1186 | LB | PhO | MeIleNH | = | T | | | | 5 | | | | | |
| 1187 | LB | HO | PheNH | = | T | | | | 3.5 | | | | | |
| 1189 | YW | PhO | CHXCH2AlaNH | = | T | | | | 0.04 | | | | | |
| 1190 | LB | HO | ValNH | = | T | | | | 0.7 | | | | | |
| 1192 | LB | HO | LeuNH | = | T | | | | 1.4 | | | | | |
| 1193 | LB | PhO | MeAlNH | = | T | [FAST ISOMER] | | | | | | | | |
| 1194 | LB | PhO | ProNH | = | T | | | | 6 | | | | | |
| 1196 | KT | PhO | MeGlutamineNH | = | T | | | | 1.2 | | | | | |
| 1197 | HWT | PhO | Me-B-AlaNH | = | T | | | | >250 | | | | | |
| 1198 | HWT | PhO | Me-GABANH | = | T | | | | >250 | | | | | |
| 1199 | HWT | PhO | MeCaproylNH | = | T | | | | >250 | | | | | |
| 1200 | HWT | PhO | MeOCOCMe2Al | = | T | | | | 0.12 | | | | | |
| 1214 | KT | PhO | MeAsparagineNH | = | T | | | | 0.6 | | | | | |
| 1215 | KT | PhO | MeTrypNH | = | T | | | | 4 | | | | | |
| 1216 | HWT | OH | B-AlaNH | = | T | | | | 0.7 | | | | | |
| 1217 | HWT | HO | CaproylNH | = | T | | | | 1.4 | | | | | |
| 1218 | PS | PhO | PntAlaNH | = | T | | | | <0.08 | | | | | |
| 1219 | PS | PhO | neoPntAlaNH | = | T | | | | <0.08 | | | | | |
| 1220 | PS | PhO | PhenethylAlaNH | = | T | | | | 0.7 | | | | | |
| 1224 | HWT | HO | GABANH | = | T | | | | 1 | | | | | |
| 1226 | PS | PhO | 1-NapthMethAlaNH | = | T | | | | <0.08 | | | | | |
| 1227 | PS | PhO | 2-NapthMethAlaNH | = | T | | | | <0.08 | | | | | |

TABLE 7

| Cpd | Init | ArO | Y | Z | B | HIV1 MT | HIV2 MT | CC50 MT | HIV1 CEM | HIV2 CEM | 2.CEM. TK | CC50 CEM | EC50 MS | MCCMS |
|---|---|---|---|---|---|---|---|---|---|---|---|---|---|---|
| 462 | PB | PhO | MeAlaNH | N3-up | T | 3.3 | 11 | 121 | 27.5 | 40 | 30 | | | |
| 499 | PB | — | — | N3-up | T | 0.9 | 2.3 | >250 | 3 | 4 | >250 | | | |
| 536 | PB | mCF3PhO | MeAlaNH | N3-up | T | 0.45 | 0.9 | 104 | 1 | 2 | 3 | | | |
| 550 | PB | 3,5Cl2PhO | MeAlaNH | N3-up | T | 0.5 | 1 | 98 | 1.4 | 3 | 12 | | | |
| 569 | PB | — | — | N3up | U | | | | >400 | >400 | >400 | | | |
| 571 | PB | PhO | MeAlaNH | N3up | U | | | | >202 | >202 | 117 | | | |
| 657 | ASS | PhO | HexNH | N3up | T | | | | >40 | >40 | >18 | | | |
| 659 | ASS | PhO | BuNH | N3up | T | | | | >42 | >42 | >42 | | | |
| 661 | ASS | PhO | C12NH | N3up | T | | | | >7 | >7 | >7 | | | |
| 687 | DC | — | — | N3-up | BzT | | | | 2.5 | 2.8 | >100 | >100 | | |
| 731 | DC | PhO | BzAlaNH | N3-up | T | | | | 0.28 | 0.7 | 1.1 | 88 | | |
| 739 | DC | MeO | MeAlaNH | N3up | T | | | | 10 | 18 | >250 | >250 | | |
| 774 | ASS | PhO | MeAlaNH | N3up | N-OctT | | | | >10 | >10 | | 15 | | |
| 777 | DC | 2,4-Br2PhO | MeAlaNh | N3up | T | | | | 0.5 | 0.55 | 0.19 | 55 | | |
| 780 | DC | F5PhO | MeAlaNH | N3up | T | | | | 23 | 33 | 100 | 106 | | |
| 846 | ASS | PhO | CNEO | N3-up | T | | | | 13 | 14 | >250 | >250 | | |
| 847 | ASS | TFEO | CNEO | N3-up | T | | | | 12 | 9 | >250 | >250 | | |
| 850 | ASS | PhO | OH | N3-up | T | | | | 18 | 9 | >250 | >250 | | |
| 855 | ASS | TFEO | OH | N3-up | T | | | | 17.5 | 17.5 | >250 | >250 | | |
| 856 | ASS | HexO | CNEO | N3-up | T | | | | 13 | 25 | >250 | >250 | | |
| 857 | ASS | HexO | OH | N3-up | T | | | | 5 | 10 | >250 | >250 | | |
| 941 | ASS | PhO | Me-D-PheNH | N3-UP | T | | | | >50 | >50 | | 115 | >100 | >100 |
| 1069 | CW | — | — | H | A | | | | 4 | 8 | 17.5 | >250 | 24.3 | >100 |
| 1071 | ASS | HO | HOC[O]AlaNH | N3-up | T | | | | 115 | 100 | 250 | >250 | >250 | >100 |
| 1093 | CW | PhO | MeAlaNH | H | A | | | | 0.016 | 0.035 | 0.055 | 2.57 | 1.95 | >20 |
| 1221 | CY | PhO | MeAlaNH | H | C | | | | 0.6 | | | | | |
| 1225 | CW | PhO | MeAlaNH | H | I | | | | 1.2 | | | | | |

In vivo Testing

Inhibitory Effects of Test Compounds on the Initiation of MSV-induced Tumour Formation in NRMI Mice and on the Survival of MSV Innoculated NMRI Mice Mice infected with Moloney Sarcoma Virus [MSV] were treated daily with either placebo, or d4T [at one of two doses] or with compound 324 at one of the same [equimolar] doses.

Two- to three-day old NMRI mice (weighing—2 gram) were innoculated subcutaneously (s.c.) in the left hind leg with 50 μl MSV (100 foci forming units, as measured by in vitro determination of the virus-induced transformation of murine C3H embryo fibroblast cells). At 4 to 5 days post-infection, tumours develop and rapidly increase in volume upon further aging of the mice. Within 10 to 12 days post-infection, mice (then weighing—5 to 6 gram) die from the viral infection. Drug treatment started 1 hour prior to infection of the virus, and further compound administration was given daily i.p. for an additional 3 days. The mean day of tumour initiation (±standard deviation) and the mean day of survival of the mice (±standard deviation) was calculated and statistical significance of the average delay of tumour formation and the mean day of survival in the treated groups versus the untreated (control) group was assessed by two-tailed student's t-test.

Whilst d4T failed to give any detectable delay in either tumour appearance or death, a significant effect on both parameters was seen with high-dose compound 324, and an effect on the first disease parameter at low dose [FIG. 1].

What is claimed is:

1. A compound of the formula:

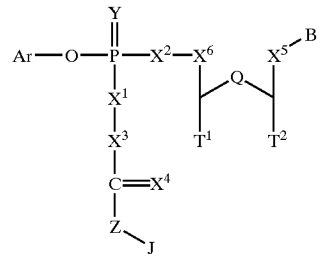

wherein:

Ar is phenyl, naphthyl, or pyridyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio;

Y is =O or =S;

$X^2$ and $X^6$ taken together are direct bond or $X^6$ is —$CH_2$— and $X^2$ is

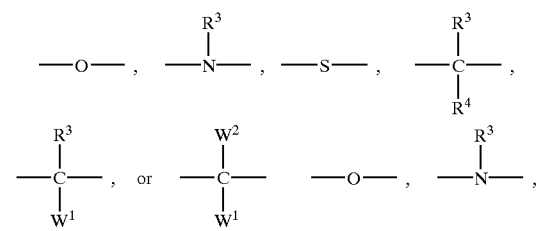

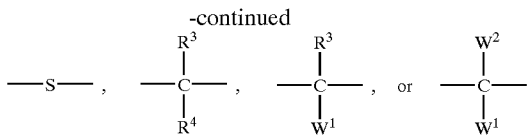

$X^3$ is alkylene of 1 to 6 carbon atoms;
$X^1$ is:
Z is

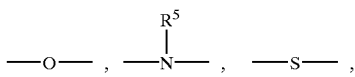

alkylene, or phenylene in which $R^5$ is hydrogen, alkyl, or phenyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio;

each of $R^3$ and $R^4$ independently is hydrogen, alkyl, or phenyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio;

$X^4$ is =O or =$CH_2$;

$X^5$ is a direct bond or —$CH_2$—;

J is hydrogen, alkyl of 1 to 16 carbon atoms, cycloalkyl of 3 to 12 carbon atoms, benzyl, phenyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio, or a heterocyclic group selected from the group consisting of pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, napthridinyl, cinnolinyl, quinazolinyl, pyridopyridyl, benzoxazinyl, quinoxalinyl, chromenyl, chromanyl, isochromanyl, and carbolinyl;

Q is

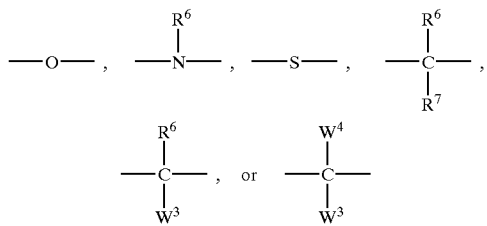

each of $R^6$ and $R^7$ independently is hydrogen, alkyl, or phenyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio;

each of $W^1$, $W^2$, $W^3$, and $W^4$ independently is fluoro, chloro, bromo, or iodo;

$T^1$ and $T^2$ taken together are:

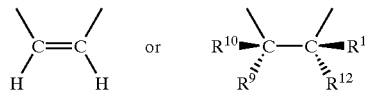

in which $R^9$ is hydrogen, halogeno, cyano, amino, CO-alkyl, or alkyl and $R^{10}$, $R^{11}$, and $R^{12}$ independently are hydrogen, azido, halogeno, cyano, amino, CO-alkyl, or alkyl; and B is a monovalent radical of unsubstituted thymine, cytosine, adenine, or guanine, or a monovalent radical of substituted uracil, thymine, cytosine, adenine, or guanine in which the substituents are selected from halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, alkylthio, alkyl, and benzyl;

or a pharmaceutically acceptable salt or ester thereof.

2. A compound according to claim 1 in which each of $X^2$ and Q is oxygen, $X^6$ is —$CH_2$—, $X^5$ is a direct bond, and $T^1$ and $T^2$ together are —CH=CH—.

3. A compound according to claim 1 in which each of $X^2$, $X^4$, Q, Y, and Z is oxygen, $X^1$ is —NH—, $X^5$ is a direct bond, $X^6$ is —$CH_2$—, and $T^1$ and $T^2$ together are —CH=CH—.

4. A compound according to claim 3 in which B is thymine.

5. A compound according to claim 1 in which each of $X^2$ and Q is oxygen, $X^6$ is —$CH_2$—, $X^5$ is a direct bond, and $T^1$ and $T^2$ taken together are:

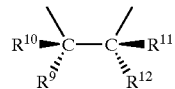

in which $R^9$, $R^{10}$, $R^{11}$, and $R^{12}$ are as therein defined.

6. A compound according to claim 5 in which B is adenine or thymine.

7. A compound according to claim 6 in which each of Y, $X^4$, and Z is oxygen, and $X^1$ is —NH—.

8. A pharmaceutical composition comprising a quantity of a compound according to claim 1 at least sufficient to produce an anti-viral effect in combination with a pharmaceutical carrier.

9. A compound of the formula

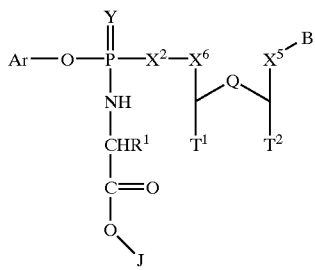

wherein:
Ar is phenyl, naphthyl, or pyridyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio;
Y is =O or =S;
$X^2$ and $X^6$ taken together are direct bond or $X^6$ is —CH$_2$— and x2 is

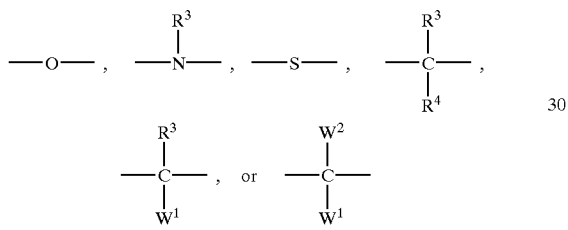

$R^1$ is hydrogen, methyl, prop-2-yl, n-butyl, but-2-yl, benzyl, 3-guanidinopropyl, carbamoylmethyl, carboxymethyl, mercaptomethyl, 2-amino-2-carboxyethyldithiomethyl, 2-carboxyethyl, 2-carbamoylethyl, 1 H-imidazolemethyl, 4-aminobutyl, 2-methylthioethyl, hydroxymethyl, 1-hydroxyethyl, 1 H-indol-3-yl-methyl, or 4-hydroxybenzyl;
each of $R^3$ and $R^4$ independently is hydrogen, alkyl, or phenyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio and each of $W^1$ and $W^2$ independently is fluoro, chloro, bromo, or iodo;
$X^5$ is a direct bond or —CH$_2$—;
J is hydrogen, alkyl of 1 to 16 carbon atoms, cycloalkyl of 3 to 12 carbon atoms, benzyl phenyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio; or a heterocyclic group selected from the group consisting of pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, napthridinyl, cinnolinyl, quinazolinyl, pyridopyridyl, benzoxazinyl, quinoxalinyl, chromenyl, chromanyl, isochromanyl, and carbolinyl;
Q is

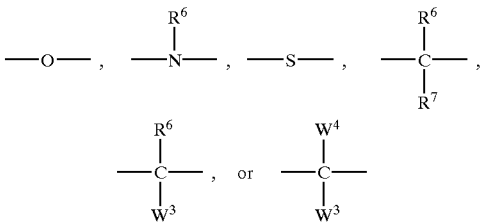

in which each of $R^6$ and $R^7$ independently is hydrogen, alkyl, or phenyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio;
each of $W^3$ and $W^4$ independently is fluoro, chloro, bromo, or iodo;
$T^1$ and $T^2$ taken together are:

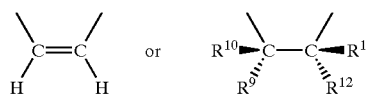

in which $R^9$ is hydrogen, halogeno, cyano, amino, CO-alkyl, or alkyl and $R^{10}$, $R^{11}$, and $R^{12}$ independently are hydrogen, azido, halogeno, cyano, amino, CO-alkyl, or alkyl; and
B is a monovalent radical of unsubstituted thymine, cytosine, adenine, or guanine, or a monovalent radical of substituted uracil, thymine, cytosine, adenine, or guanine in which the substituents are selected from halogeno, halomethyl, hydroxy, carboxy, carboxyalkyl, alkoxy, alkanoyl, alkanoyloxy, benzyloxy, benzyloyl, benzoyloxy, amino, alkylamino, dialkylamino, cyano, azido, nitro, mercapto, alkylthio, alkyl, and benzyl;
or a pharmaceutically acceptable salt or ester thereof.

10. A compound according to claim 9 in which each of $X^2$ and Q is oxygen, $X^6$ is —CH$_2$—, $X^5$ is a direct bond, and $T^1$ and T2 together are —CH=CH—.

11. A compound according to claim 10 in which each of $X^4$ and Y is oxygen.

12. A compound according to claim 11 in which B is thymine.

13. A compound according to claim 9 in which each of $X^2$ and Q is oxygen, $X^6$ is —CH$_2$—, $X^5$ is a direct bond, and $T^1$ and $T^2$ taken together are:

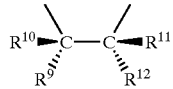

in which $R^9$, $R^{10}$, $R^{11}$, and $R^{12}$ are as therein defined.

14. A compound according to claim 13 in which B is adenine or thymine.

15. A compound according to claim 14 in which each of Y and $X^4$ is oxygen.

16. A compound according to claim 9 having the formula:

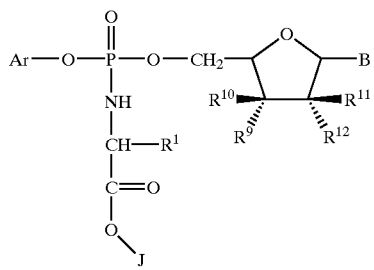

in which

Ar is phenyl, unsubstituted or substituted with chloro, bromo, fluoro, trifluoromethyl, methyl or ethyl, $R^1$ is hydrogen, methyl, prop-2-yl, n-butyl, but-2-yl, benzyl, 3-guanidinopropyl, carbamoylmethyl, carboxymethyl, mercaptomethyl, 2-amino-2-carboxyethyidithiomethyl, 2-carboxyethyl, 2-carbamoylethyl, 1H-imidazolemethyl, 4-aminobutyl, 2-methylthioethyl, hydroxymethyl, 1-hydroxyethyl, 1H-indol-3-yl-methyl, or 4-hydroxybenzyl; preferably 1 substituent. Substituents include halo, halomethyl (such as $CF_3$ and $CCl_3$), oxo, hydroxy, carboxy, carboxyalkyl, alkoxy, alkanoyl, alkanoyloxy, aryloxy, aryloyl, aryloyloxy, amino, alkylamino, dialkylamino, cyano, azide, nitro, thiol, alkylthiol, sulphonyl, sulphoxide, heterocyclic, alkyl, benzyl, and aryl (such as phenyl and substituted phenyl). B is a monovalent radical of unsubstituted thymine, cytosine, adenine, or guanine, or a monovalent radical of substituted uracil, thymine, cytosine, adenine, or guanine in which the substituents are as defined above; e.g., halo, halomethyl, oxo, hydroxy, carboxy, carboxyalkyl, alkoxy, alkanoyl, alkanoyloxy, aryloxy, aryloyl, aryloyloxy, amino, alkylamino, dialkylamino, cyano, azide, nitro, thiol, alkylthiol, sulphonyl, sulphoxide, heterocyclic, alkyl, benzyl, and aryl.

Preferably, B is adenine or thymine naturally occurring amino acid such as alanine ($R^1$ is methyl), arginine ($R^1$ is 3-guanidinopropyl), asparagine ($R^1$ is carbamoylmethyl), aspartic acid ($R^1$ is carboxymethyl), cysteine ($R^1$ is mercaptomethyl), cystine ($R^1$ is 2-amino-2-carboxyethyidithiomethyl), glycine ($R^1$ is hydrogen), glutamic acid ($R^1$ is 2-carboxyethyl), glutamine ($R^1$ is 2-carbamoylethyl), histidine ($R^1$ is 1 H-imidazolemethyl), isoleucine ($R^1$ is but-2-yl), leucine ($R^1$ is butyl), lysine ($R^1$ is 4-aminobutyl), methionine ($R^1$ is 2-methylthioethyl), phenylalanine ($R^1$ is benzyl), serine ($R^1$ is hydroxymethyl), threonine ($R^1$ is 1-hydroxyethyl), tryptophan ($R^1$ is 1H-indol-3-ylmethyl), tyrosine ($R^1$ is 4-hydroxybenzyl), and valine ($R^1$ is prop-2-yl).

Preferably $R^1$ is "$X^3$ is a $C_{1-6}$ alkylene group, $X^3$ may be a $C_{1-6}$ substituted or unsubstituted, branched or unbranched, methylene chain,"

B is adenine or thymine, and

J, $R^9$, $R^{10}$, $R^{11}$, and $R^{12}$ are as therein defined.

17. A compound according to claim 16 in which J is hydrogen.

18. A compound according to claim 16 in which B is thymine.

19. The compound having the formula:

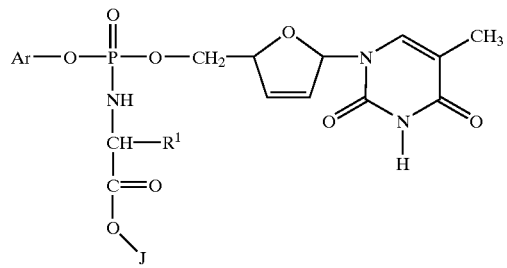

in which Ar is 4-ethylphenyl, $R^1$ is methyl, and J is methyl; in which Ar is phenyl, $R^1$ is methyl, and J is methyl; in which Ar is 4-fluorophenyl, $R^1$ is methyl, and J is methyl; in which Ar is 3-trifluoromethylphenyl, $R^1$ is methyl, and J is methyl; in which Ar is 3,5-dichlorophenyl, $R^1$ is methyl, and J is methyl; in which Ar is phenyl, $R^1$ is methyl, and J is benzyl; in which Ar is 2,4-dibromophenyl, $R^1$ is methyl, and J is methyl; in which Ar is pentafluorophenyl, $R^1$ is methyl, and J is methyl; in which Ar is phenyl, $R^1$ is methyl, and J is hexyl; in which Ar is phenyl, $R^1$ is benzyl, and J is methyl; in which Ar is phenyl, $R^1$ is but-2-yl, and J is methyl; in which Ar is phenyl, $R^1$ is prop-2-yl, and J is methyl; in which Ar is phenyl, $R^1$ is hydrogen, and J is methyl; in which Ar is phenyl, $R^1$ is 2-methylthioethyl, and J is methyl; in which Ar is 2,4-dibromophenyl, $R^1$ is methyl, and J is benzyl; in which Ar is phenyl, $R^1$ is benzyl, and J is benzyl; in which Ar is phenyl, $R^1$ is benzyl, and J is tert.-butyl; in which Ar is phenyl, $R^1$ is methyl, and J is cyclohexyl; in which Ar is phenyl, $R^1$ is methyl, and J is tert.-butyl; in which Ar is phenyl, $R^1$ is carboxymethyl, and J is methyl; in which Ar is phenyl, $R^1$ is 3-guanidinopropyl, and J is methyl; in which Ar is phenyl, $R^1$ is methyl, and J is n-pentyl; in which Ar is phenyl, $R^1$ is methyl, and J is 2,2-dimethylpropyl; in which Ar is phenyl, $R^1$ is methyl, and J is 1-naphthyl; or in which Ar is phenyl, $R^1$ is methyl, and J is 2-naphthyl.

20. A compound of the formula:

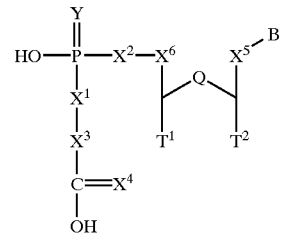

wherein:

Y is $=O$ or $=S$;

$X^1$ is:

$X^2$ and $X^6$ taken together are direct bond or $X^6$ is —$CH_2$—; and $X^2$ is

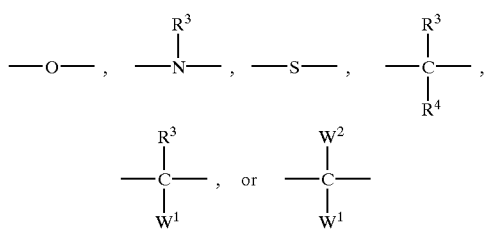

in which each of $R^3$ and $R^4$ independently is hydrogen, alkyl, or aryl and each of $R^3$ and $R^4$ independently is hydrogen, alkyl, or phenyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio;

$X^3$ is (i) alkylene of 1 to 6 carbon atoms, or (ii) $CHR^1$ in which $R^1$ is 3-guanidinopropyl, mercaptomethyl, 2-amino-2-carboxyethyldithiomethyl, carboxymethyl, 2-carboxyethyl, carbamoylmethyl, 2-carbamoylethyl, 1H-imidazolemethyl, 4-aminobutyl, 2-methylthioethyl, hydroxymethyl, 1-hydroxyethyl, 1H-indol-3-ylmethyl, benzyl, or 4-hydroxybenzyl;

$X^4$ is =O or =$CH_2$;

$X^5$ is a direct bond or —$CH_2$—;

Q is

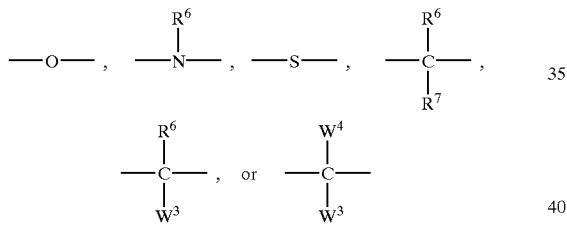

each of $R^6$ and $R^7$ independently is hydrogen, alkyl, or phenyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio, and each of $W^1$, $W^2$, $W^3$, and $W^4$ independently is fluoro, chloro, bromo, or iodo;

$T^1$ and $T^2$ taken together are:

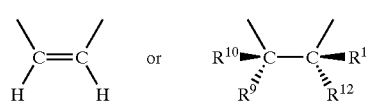

in which $R^9$ is hydrogen, halo, cyano, amino, CO-alkyl, or alkyl and $R^{10}$, $R^{11}$, and $R^{12}$ independently are hydrogen, azido, halo, amino, CO-alkyl, or alkyl; and B is a monovalent radical of unsubstituted thymine, cytosine, adenine, or guanine, or a monovalent radical of substituted uracil, thymine, cytosine, adenine, or guanine in which the substituents are selected from halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, alkylthio, alkyl, and benzyl;

or a pharmaceutically acceptable salt or ester thereof.

21. A compound according to claim 20 in which each of Y and $X^4$ is oxygen, $X^1$ is —NH—, and $X^3$ is —$CHR^1$—.

22. A pharmaceutical composition comprising a quantity of a compound according to claim 9 least sufficient to produce an anti-viral effect in combination with a pharmaceutical carrier.

23. compound of the formula:

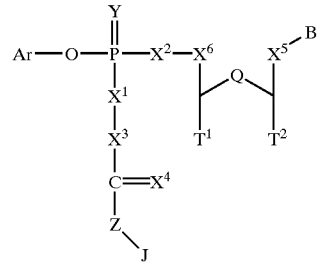

wherein:

Ar is phenyl, naphthyl, or pyridyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio;

Y is =O or =S;

$X^2$ and $X^6$ taken together are direct bond or $X^6$ is —$CH_2$— and $X^2$ is

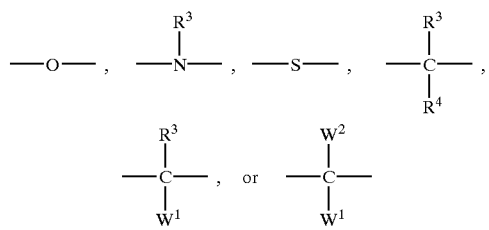

$X^3$ is —$CR^1R^2$— in which each of $R^1$ and $R^2$ is hydrogen, alkyl of 1 to 6 carbon atoms, or phenyl;

$X^1$ is:

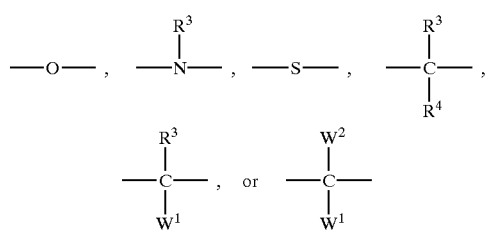

Z is

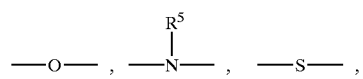

alkylene, or phenylene in which $R^5$ is hydrogen, alkyl, or phenyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio;

each of $R^3$ and $R^4$ independently is hydrogen, alkyl, or phenyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio;

$X^4$ is $=O$ or $=CH_2$;

$X^5$ is a direct bond or $-CH_2-$;

J is hydrogen, alkyl of 1 to 16 carbon atoms, cycloalkyl of 3 to 12 carbon atoms, benzyl, phenyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio, or a heterocyclic group selected from the group consisting of pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, napthridinyl, cinnolinyl, quinazolinyl, pyridopyridyl, benzoxazinyl, quinoxalinyl, chromenyl, chromanyl, isochromanyl, and carbolinyl;

Q is

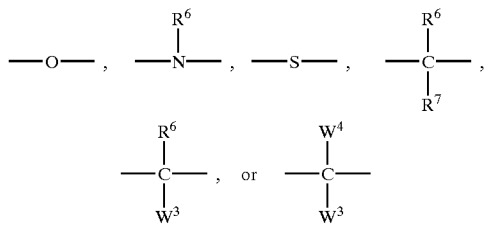

each of $R^6$ and $R^7$ independently is hydrogen, alkyl, or phenyl, unsubstituted or substituted with from 1 to 3 substituents selected from the group consisting of halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, and alkylthio;

each of $W^1$, $W^2$, $W^3$, and $W^4$ independently is fluoro, chloro, bromo, or iodo;

$T^1$ and $T^2$ taken together are:

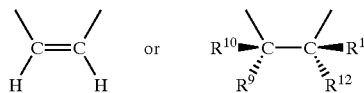

in which $R^9$ is hydrogen, halogeno, cyano, amino, CO-alkyl, or alkyl and $R^{10}$, $R^{11}$, and $R^{12}$ independently are hydrogen, azido, halogeno, cyano, amino, CO-alkyl, or alkyl; and B is a monovalent radical of unsubstituted thymine, cytosine, adenine, or guanine, or a monovalent radical of substituted uracil, thymine, cytosine, adenine, or guanine in which the substituents are selected from halogeno, halomethyl, hydroxy, carboxy, carboxyalkyl, alkoxy, alkanoyl, alkanoyloxy, phenoxy, benzoyl, benzoyloxy, amino, alkylamino, dialkylamino, cyano, azido, nitro, mercapto, alkylthio, alkyl, and benzyl;

or a pharmaceutically acceptable salt or ester thereof.

24. A compound according to claim 23 in which $R^1$ is hydrogen, each of $X^2$ and Q is oxygen, $X^6$ is $-CH_2-$, $X^5$ is a direct bond, and $T^1$ and $T^2$ together are $-CH=CH-$.

25. A compound according to claim 23 in which $R^1$ is hydrogen, each of $X^2$, $X^4$, Q, Y, and Z is oxygen, $X^1$ is $-NH-$, $X^5$ is a direct bond, $X^6$ is $-CH_2-$, and $T^1$ and T2 together are $-CH=CH-$.

26. A compound according to claim 25 in which B is thymine.

27. A compound according to claim 23 in which $R^1$ is hydrogen, each of $X^2$ and Q is oxygen, $X^6$ is $-CH_2-$, $X^5$ is a direct bond, and $T^1$ and $T^2$ taken together are:

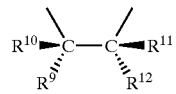

in which $R^9$, $R^{10}$, $R^{11}$, and $R^{12}$ are as therein defined.

28. A compound according to claim 27 in which B is adenine or thymine.

29. A compound according to claim 28 in which each of Y, $X^4$, and Z is oxygen, and $X^1$ is $-NH-$.

30. A pharmaceutical composition comprising a quantity of a compound according to claim 23 at least sufficient to produce an anti-viral effect in combination with a pharmaceutical carrier.

31. A compound according to claim 21 in which each of $X^2$ and Q is oxygen, $X^6$ is $-CH_2-$, $X^5$ is a direct bond, and $T^1$ and $T^2$ together are $-CH=CH-$.

32. A compound according to claim 31 in which B is thymine.

33. A compound according to claim 31 in which $R^1$ is hydrogen, methyl, prop-2-yl, n-butyl, but-2-yl, hydroxymethyl, mercaptomethyl, 1-hydroxyethyl, 2-methylthioetyhyl, carboxymethyl, 2-carboxyethyl, carbamoylmethyl, 2-carbamoylethyl, 4-aminobutyl, benzyl, 4-hydroxbenzyl, 3-guanidinopropyl, 2-amino-2-carboxyethyldithiomethyl, 1-H-imidazolemethyl, or 1H-indol-3-ylmethyl.

* * * * *